(12) United States Patent
Nelson et al.

(10) Patent No.: US 7,275,537 B2
(45) Date of Patent: Oct. 2, 2007

(54) DEVICE FOR DELIVERING PHYSIOLOGICALLY ACTIVE AGENT IN POWDERED FORM

(75) Inventors: Craig Harvey Nelson, Melbourn (GB);
Jeffrey Martin, Melbourn (GB);
Andrew Peter Scudamore, Melbourn (GB)

(73) Assignee: Meridica Limited, London (GB)

( * ) Notice: Subject to any disclaimer, the term of this patent is extended or adjusted under 35 U.S.C. 154(b) by 438 days.

(21) Appl. No.: 10/344,130

(22) PCT Filed: Aug. 8, 2001

(86) PCT No.: PCT/GB01/03555

§ 371 (c)(1),
(2), (4) Date: Jun. 6, 2003

(87) PCT Pub. No.: WO02/11800

PCT Pub. Date: Feb. 14, 2002

(65) Prior Publication Data

US 2003/0183230 A1    Oct. 2, 2003

(30) Foreign Application Priority Data

Aug. 10, 2000    (GB)    ................................ 0019715.2

(51) Int. Cl.
*A61M 15/00*    (2006.01)
*A61M 16/00*    (2006.01)

(52) U.S. Cl. .......................... 128/203.15; 128/203.19; 128/205.13

(58) Field of Classification Search ........... 128/203.15, 128/203.18, 203.19, 203.21, 200.14, 200.21, 128/200.22, 200.23, 203.22, 204.12, 205.13, 128/205.16, 206.11, 207.18, 205.15
See application file for complete search history.

(56) References Cited

U.S. PATENT DOCUMENTS

| | | | | |
|---|---|---|---|---|
| 3,921,637 A * | 11/1975 | Bennie et al. | ......... | 128/203.15 |
| 4,274,403 A | 6/1981 | Struve | | |
| 5,161,524 A * | 11/1992 | Evans | .................... | 128/203.15 |
| 5,323,936 A | 6/1994 | Wolter et al. | | |
| 5,619,984 A | 4/1997 | Hodson et al. | | |
| 5,702,362 A | 12/1997 | Herold et al. | | |
| 5,740,792 A | 4/1998 | Ashley et al. | | |
| 5,778,873 A * | 7/1998 | Braithwaite | ............ | 128/203.15 |
| 5,816,504 A | 10/1998 | Zuckschwerdt et al. | | |
| 5,921,237 A | 7/1999 | Eisele et al. | | |
| 6,612,302 B1 * | 9/2003 | Rand | ..................... | 128/200.14 |
| 6,752,147 B1 * | 6/2004 | Goldemann et al. | ... | 128/203.15 |
| 6,880,555 B1 * | 4/2005 | Brunnberg et al. | .... | 128/203.12 |
| 2004/0035420 A1 * | 2/2004 | Davies et al. | .......... | 128/203.15 |
| 2005/0081853 A1 * | 4/2005 | Young et al. | .......... | 128/203.21 |

FOREIGN PATENT DOCUMENTS

GB    2251898 A    7/1999

(Continued)

*Primary Examiner*—Teena Mitchell
(74) *Attorney, Agent, or Firm*—Foley & Lardner LLP

(57) ABSTRACT

A powder delivery device for the delivery into a patient's nasal cavity of a physiologically active agent in powdered form. A closure restricts the unwanted ingress of moisture into the device when the device is not in use. The action of opening or closing this closure may be linked to charging an air reservoir with air and/or moving a fresh powder-containing receptacle into communication with a powder delivery passage.

25 Claims, 16 Drawing Sheets

FOREIGN PATENT DOCUMENTS

| | | |
|---|---|---|
| JP | 10-028735 | 2/1998 |
| WO | EP 0341967 A2 | 11/1989 |
| WO | WO92/04928 | 4/1992 |
| WO | WO92/06727 | 4/1992 |
| WO | EP 0518087 A1 | 12/1992 |
| WO | WO93/03782 | 3/1993 |
| WO | WO93/09832 | 5/1993 |
| WO | WO94/05359 | 3/1994 |
| WO | WO94/11044 | 5/1994 |
| WO | WO98/30262 | 7/1998 |
| WO | WO98/34732 | 8/1998 |
| WO | WO 01/26120 * | 4/2001 |

* cited by examiner

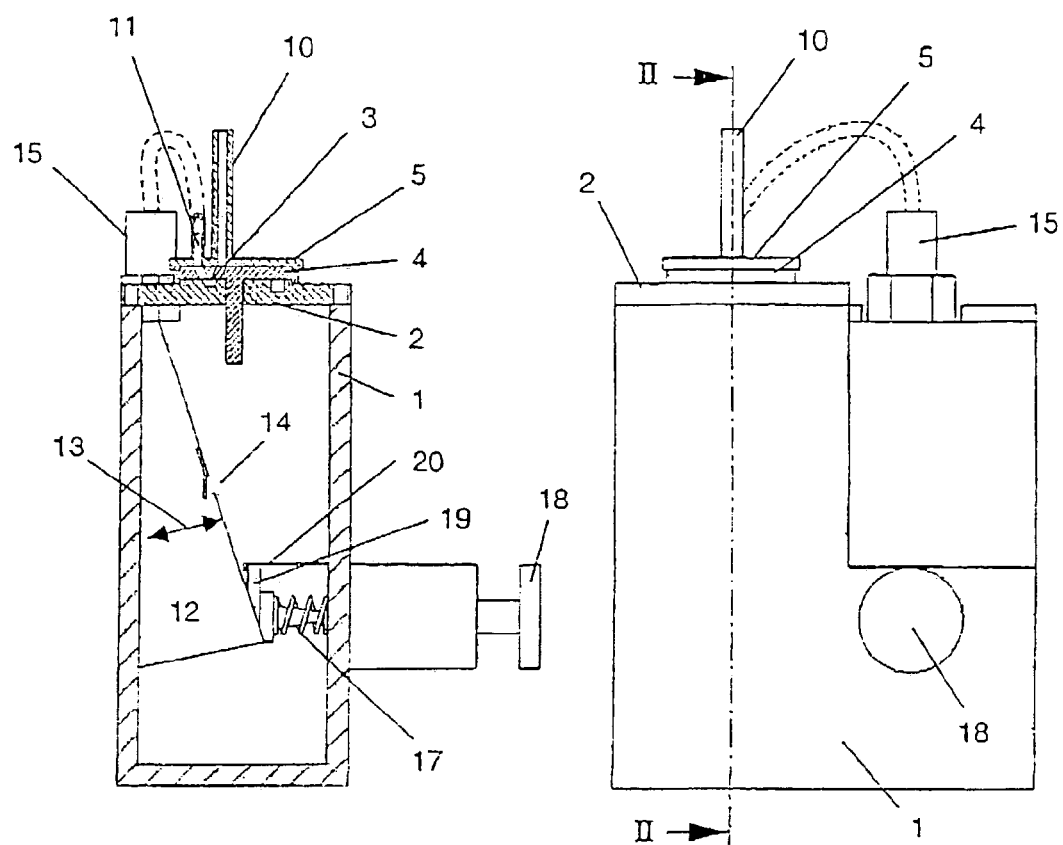
Fig 2
Fig 3
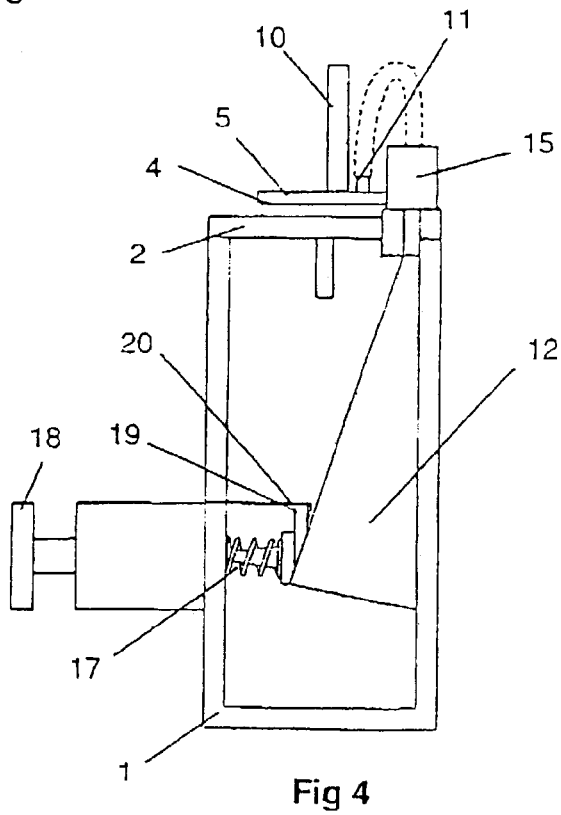
Fig 4

DEVICE FOR DELIVERING PHYSIOLOGICALLY ACTIVE AGENT IN POWDERED FORM

This invention relates to a device for delivering a physiologically active agent in powdered form, particularly but not exclusively to a device for delivering multiple doses of physiologically active agent in powdered form. The device is preferably, but not exclusively, intended for the delivery of a physiologically active agent in powdered form into a patient's nasal cavity.

BACKGROUND

The term "physiologically active agent" used hereinafter includes any compound or composition of matter which, when administered to an organism (human or animal subject) induces a desired pharmacologic and/or physiologic effect by local and/or systemic action. The term therefore includes those compounds or chemicals traditionally regarded as drugs, biopharmaceuticals (including molecules such as peptides, proteins, nucleic acids), vaccines and gene therapies (e.g. gene constructs). When the agent is provided in powdered form, the size of the powder is affected by its delivery route. For pulmonary delivery the optimum particle size is 1-5 μm, whereas for nasal delivery the optimum size is believed to be 10-20 μm. A suitable amount for a single dosing event is of the order of 100's of μg to 10's of mg.

It has been recognised that nasal delivery provides an excellent route for delivering some physiologically active agents into the human system in addition to topical treatment. For example, advantages of nasal delivery include high permeability of the nasal cavity compared with the gastro-intestinal tract, the highly vascularised subepithelial layer in the nasal mucosa and high patient compliance compared with injection. This can lead to potentially greater therapeutic effect, the requirement for potentially smaller doses and rapid systemic absorption. There is a demand amongst pharmaceutical companies for nasal drug delivery devices which have some of the following properties: smaller delivery volumes, increased dosing accuracy, an avoidance for a need to prime device, prevention of bacteriological contamination and performance that is independent of the user.

Dry powders of physiologically active agents generally offer advantages over liquid formulations in nasal delivery, these advantages including longer retention in the nasal cavity, better absorption of some agents, use of higher concentrations of agent, minimisation of problems associated with liquid running back out of the nose and improved stability of the physiologically active agent when stored in dry form.

SUMMARY

According to a first aspect of the present invention there is provided a device for delivering multiple doses of physiologically active agent in powdered form, the device comprising a bulk reservoir for containing multiple doses of powder, a powder delivery passage for the forced flow therealong to a patient of gas with a dose of said powder entrained therein, a closure for restricting the unwanted ingress of moisture into the device via said passage when the device is not in use, and a powder metering unit for metering out a dose of powder from said bulk reservoir and then aligning said metered dose with said gas flow passage, the device being so constructed and arranged that said metering unit is operated by the action of opening or closing said closure.

In those hereinafter described and illustrated preferred embodiments of device which are in accordance with the first aspect of the present invention, metering of the powder is based on the filling of a recess with a repeatable mass of powder. The metering is carried out by completely filling a fixed volume recess with powder. This assumes the powder density does not change during the lifetime of the device. In these embodiments the powder is dosed into a recess of the powder metering unit under gravity. Several other options exist for encouraging the powder into the recess, including air pressure (either pushing or sucking the powder into the metering unit's recess) and by applying mechanical force, for example by scraping.

In those hereinafter described and illustrated preferred embodiments of device which are in accordance with the fast aspect of the present invention, the metering unit comprises a movable element with a recess formed therein to receive powder from the bulk reservoir. The size of this recess corresponds to the size of the metered dose. The element is movable between a first position, in which the recess can receive powder from a powder exit of the bulk reservoir and is separated from the powder delivery passage, and a second position. This second position is displaced from the first position. In this second position the recess is aligned with the powder delivery passage and is separated tom the powder exit.

In those preferred embodiments of device which are in accordance with the first aspect of the present invention, the slidable element is constrained to move generally linearly and is anchored to another part of the device by a linkage, which linkage is arranged to be manipulated by the opening of the closure to move the slidable element.

In the preferred embodiments of device which are in accordance with the first aspect of the present invention, the operation of the powder metering unit is thus performed automatically by the operator of the device (usually the intended recipient or patient) opening the closure, which action the person will have to perform in any event. In removing the need for that person to conduct a conscious, discrete action of operating the powder metering unit (separately of the act of opening or closing the closure), use of the device is simplified.

According to a second aspect of the present invention there is provided a powder delivery device for the delivery into a patient's nasal cavity of a physiologically active agent in powdered form, the device comprising a manually rechargeable as reservoir, a passage from said air reservoir terminating as a nasal tube for insertion into the nostril of the patient, a closure for restricting the unwanted ingress of moisture into the device via said passage when the device is not in use, and a powder receiving section associated with said passage, whereby the rapid release of a charge of air from said reservoir along said passage will take a dose of powder from said section and entrain it in said released charge of air before expelling it from the nasal tube, wherein the air reservoir is constructed and arranged to be charged with air by the action of opening or closing said closure.

By linking the charging of the manually rechargeable air reservoir with an action which will clearly have to be performed before the device is used (namely opening or closing the closure), the need for the person preparing the device for use to have to carry out a dedicated, discrete action of "priming" the air reservoir is avoided. Once again, this has advantages in terms of simplifying use of the device.

According to a third aspect of he present invention there is provided a device for delivering multiple doses of physiologically active agent in powdered form, the device comprising:

an upstream air supply passage for the forced flow therealong of air;

a downstream powder delivery passage for the forced flow therealong of air with powder entrained therein; and a drug metering slide having first and second parallel planar faces with a powder-containing recess recessed in one of said faces, said recess opening only into said one face;

wherein said upstream and downstream passages are not connected when said slide is in a first position and said slide is slidable from said first position to a second position in which said upstream and downstream passages are connected via said recess whereby, when the recess is filled with powder, the forced flow of air into said recess from said upstream passage will displace the powder from said recess and cause it to exit the recess though said downstream passage entrained in the forced air flow.

In those hereinafter described and illustrated preferred embodiments of device which are in accordance with the third aspect of the present invention, the metered dose of powder effectively blocks the passage of air from the air reservoir. Consequently, upon activation of the device displacement of the powder from the recess, and its entrainment in the air, is highly efficient leaving substantially no residual powder in the recess to upset the dosing accuracy.

According to a fourth aspect of the present invention there is provided a device for delivering multiple doses of physiologically active agent in powdered form, the device comprising a manually rechargeable air reservoir, an air intake for the aspiration of air into said air reservoir upon recharging of said air reservoir, an air exit passage from said air reservoir, and a powder receiving section associated with said exit passage, whereby the rapid release of a charge of air from said reservoir along said exit passage will take a dose of powder from said station and entrain it in said released charge of air before expelling it via the exit passage, wherein the device further comprises a single openable closure for restricting the unwanted ingress of moisture into the device via said exit passage and via said air intake when the device is not in use and the closure is closed.

An important requirement for a device for use in delivering physiologically active agent in powdered form is to ensure adequate sealing of the device to avoid moisture ingress. Moisture ingress can potentially affect the delivered dose of the agent by coating surfaces and causing agglomeration of the powder.

In those hereinafter described and illustrated preferred embodiments of device which are in accordance with the fourth aspect of the present invention, the closure not only prevents loose material from entering the exit passage of the device, but also provides a seal against moisture entering the device via the exit passage and the air intake.

In preferred arrangements of the fourth aspect of the invention, opening or closing of the closure may also be used to operate a powder metering unit (as in tie first aspect of the present invention) and/or to recharge an air reservoir (as in the second aspect of the present invention).

By causing other actions within the device to be driven by the unavoidable action of manipulating the closure, a device can be provided which is easy to use, by virtue of minimising the number of discrete actions which the intended user of the device has consciously to perform prior to being able to use the device to discharge powder.

According to a fifth aspect of the present invention there is provided a device for delivering multiple doses of physiologically active agent in powdered form, the device comprising a powder container defining therein a plurality of individual receptacles, each receptacle containing a discrete metered dose of powder, a powder delivery passage for the forced flow therealong to a patient of gas with a said metered dose of powder entrained therein so as substantially to empty a said receptacle, a closure for restricting the unwanted ingress of moisture into the device via said passage when the device is not in use, and a container indexing mechanism for indexing movement of said container to move a substantially empty said receptacle out of communication with said powder delivery passage and to move a flesh powder-containing said receptacle into communication with said powder delivery passage, the device being so constructed and arranged that said container indexing mechanism is operated by the action of opening or closing said closure.

By providing the doses of powder as discrete pre-metered doses, the need to meter out doses of powder within the device can be avoided. Doses pre-metered in a factory environment, rather than in the device itself, may be easier to meter accurately. Furthermore, the arrangement of the device may be such that the powder in each discrete metered dose is sealed against attack from moisture except immediately prior to its administration.

BRIEF DESCRIPTION OF THE DRAWINGS

Embodiments of device in accordance with the different aspects of the present invention will now be described, by way of example only, with reference to the accompanying drawings, in which:

FIG. 2 is a vertical cross-section of the FIG. 1 device, taken along the line II-II in FIG. 3;

FIG. 3 is a front elevation of the device of FIG. 1;

FIG. 4 is a side elevation of the device of FIG. 1;

DETAILED DESCRIPTION

Figure 1:
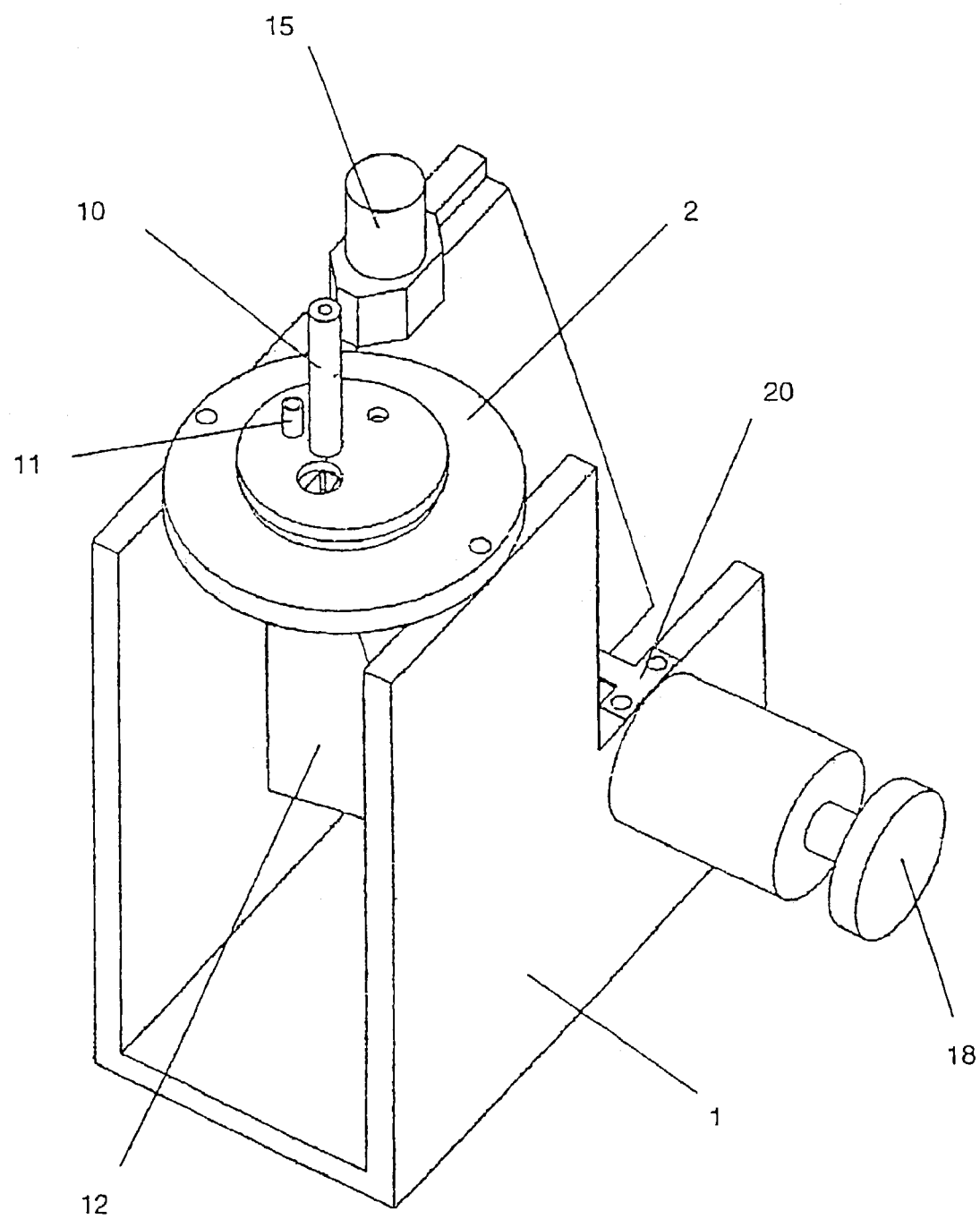
FIG. 1 is a perceive view of a first embodiment of device for use in delivering multiple doses of physiologically active agent in powdered form.
Figure 6:
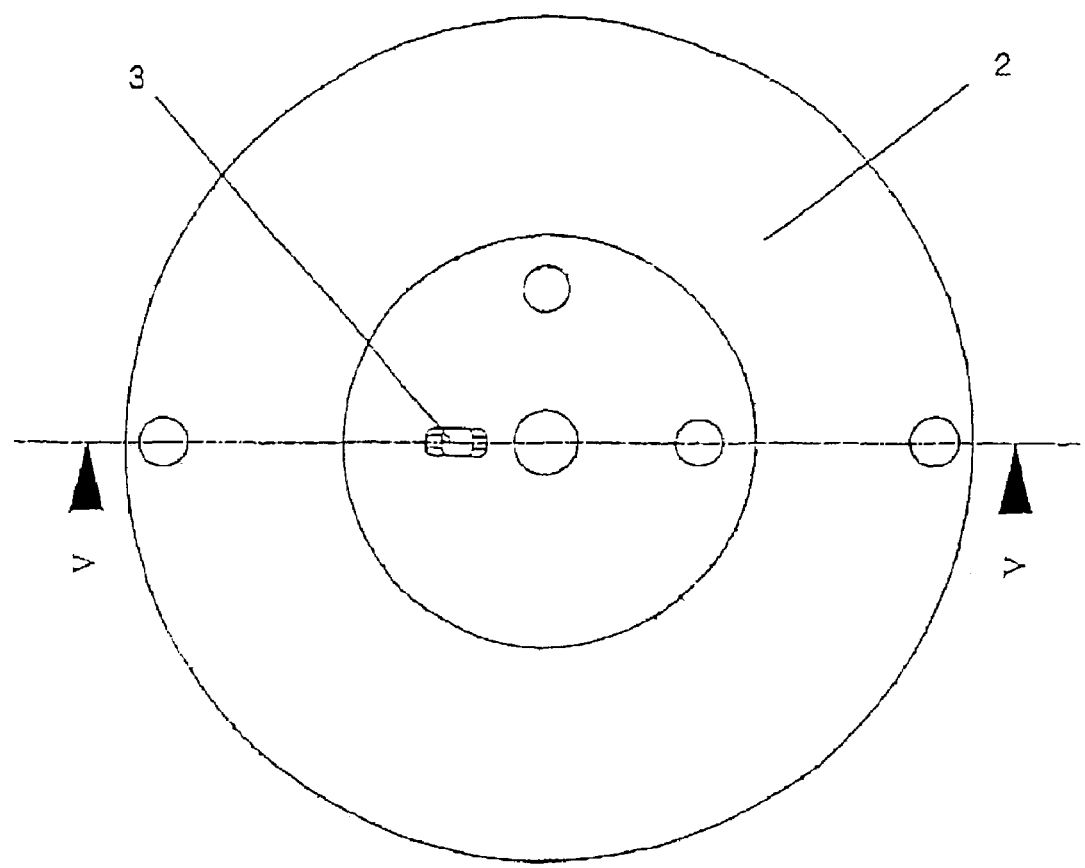
FIG. 6 is a top plan view of the top plate of the first embodiment.
Figure 5:
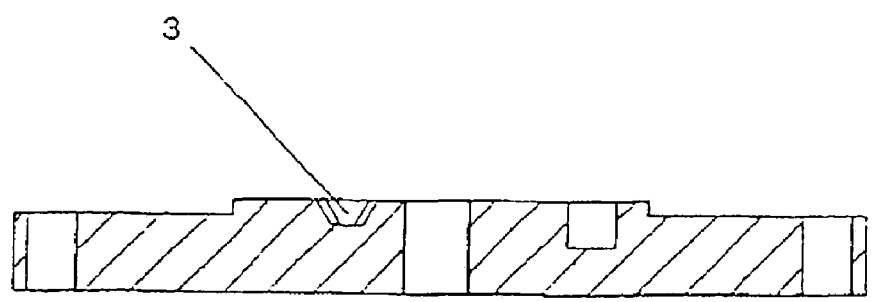
FIG. 5 is a cross-sectional side elevations taken along the line V-V in FIG. 6, of the top plate of the embodiment of FIG. 1.
Figure 8:
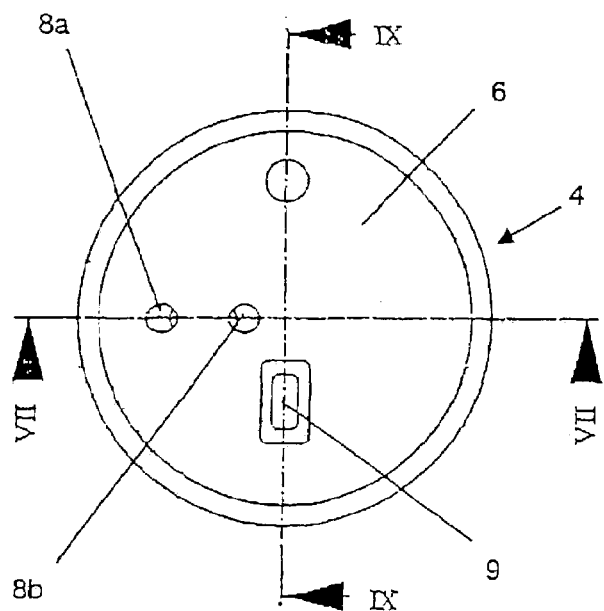
FIG. 8 is a top plan view of the spacer plate of the first embodiment.
Figure 9:
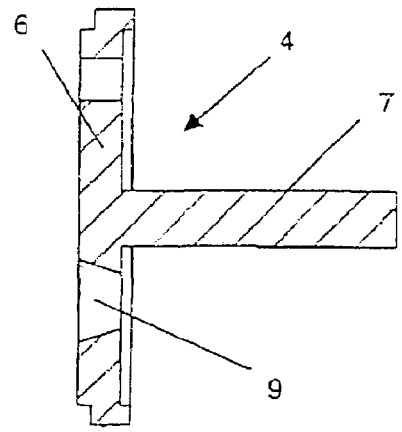
FIG. 9 is a cross-sectional side elevation, taken along the line IX-IX of FIG. 8.
Figure 7:
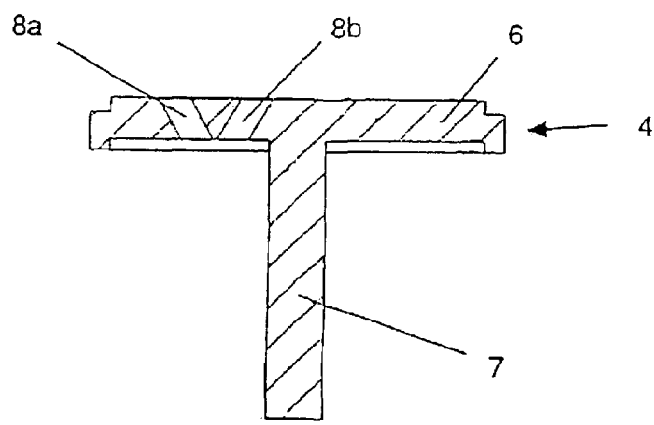
FIG. 7 is a cross-sectional side elevation of the spacer plate of the first embodiment, taken along the line VII-VII of FIG. 8.
Figure 11:
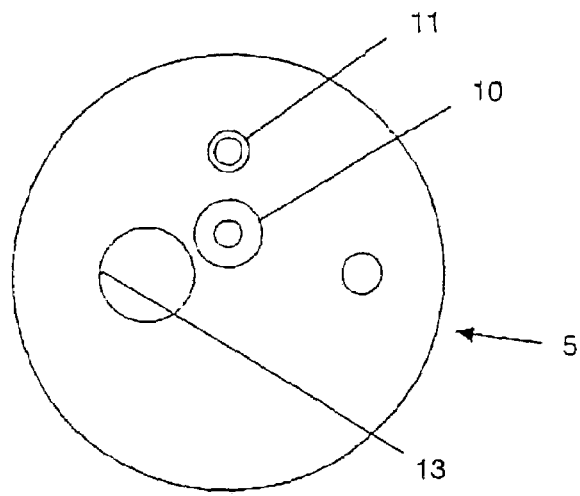
FIG. 11 is a top plan view of the nozzle plate of FIG. 10.
Figure 10:
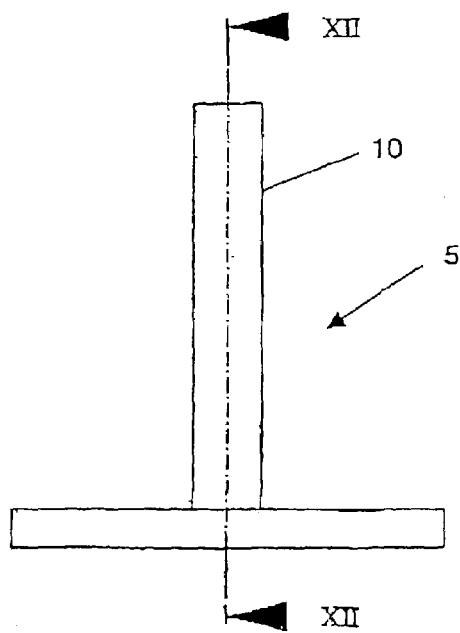
FIG. 10 is a side elevation of the nozzle plate of the first embodiment.
Figure 12:
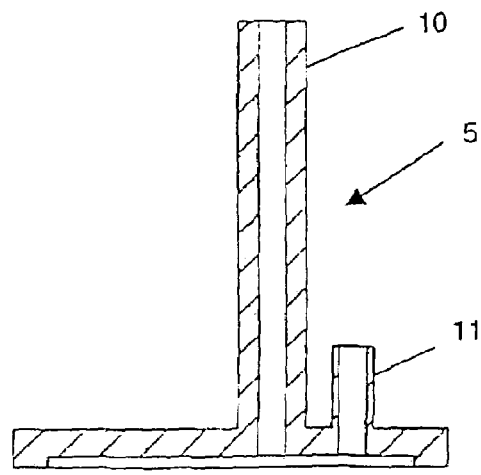
FIG. 12 is a cross-sectional side elevation of the top plate, taken along the line XII-XII of FIG. 10.
Figure 13:
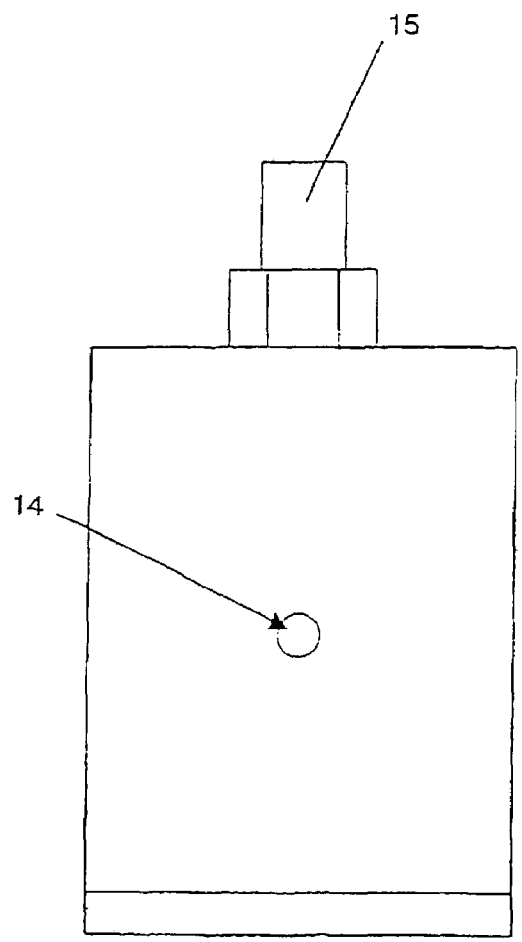
FIG. 13 is a front elevation of the bellows of the first embodiment.
Figure 14:
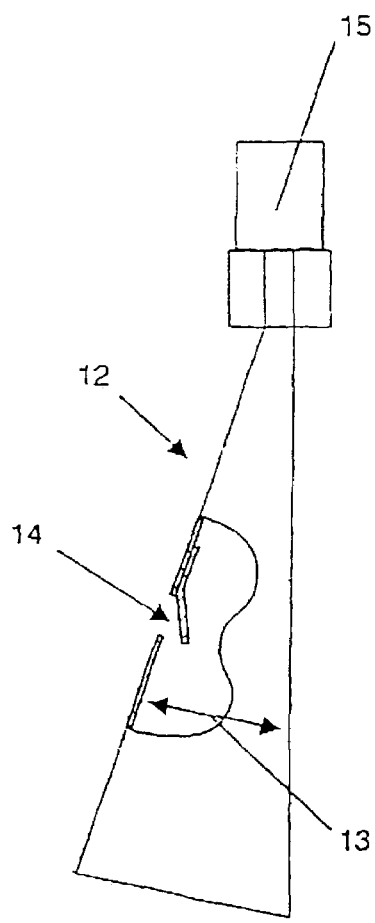
FIG. 14 is a side elevation of the bellows of FIG. 13.

FIGS. 1-14 of the drawings illustrate a bench prototype (and components thereof) of a first embodiment of device suitable for delivering multiple doses of physiologically active agent in powdered form, built to test some of the principles involved. It is anticipated that, as in the later embodiments, the finished device will be capable of being reduced in size to be hand-held in use, and capable of being stored in a pocket or handbag when not in use. FIG. 19 onwards illustrate more compact, hand-held devices.

In the embodiment illustrated in FIGS. 1-14, the device comprises a frame 1 of generally U-shaped cross section—see FIGS. 1 and 2. Secured to the top of the frame 1 is a top plate 2 having a recess 3 formed in its top planar surface. This recess 3 is generally cup-shaped and can be seen most clearly in FIG. 5. The top plate 2 combines with a spacer plate 4 and a nozzle plate 5 to form a powder metering unit for metering out a dose of powder from a bulk reservoir containing multiple doses of powder.

The spacer plate 4 includes a main circular element 6 with a cylindrical hub 7 downwardly depending therefrom, as shown in FIG. 7. The cylindrical hub 7 is rotatably received in a bore provided in the top plate 2, to enable the spacer plate 4 (and nozzle plate 5 mounted thereon) to be rotatably indexed relative to the top plate 2 around the longitudinal axis of the hub 7, for reasons which will be explained later.

Provided in the main circular element 6 are two angled drillings 8*a*, 8*b* aligned on a line radial to the longitudinal axis of the cylindrical hub 7. Spaced 90° therefrom with regard to said longitudinal axis, the main circular element 6 is also provided with an aperture 9 which converges downwardly in tie manner of a hopper.

The nozzle plate 5 is mounted on top of the plate 4 and is rotationally fast therewith. The space plate 4 and nozzle plate 5 were made separately in the embodiment of FIGS. 1-14 purely for ease of manufacture. The nozzle plate 5 has two stub pipes 10,11 extending upwardly therefrom and positioned on a radial line with respect to the longitudinal axis of the cylindrical hub 7 of the spacer plate 4. The longest stub pipe models a nasal tube for insertion into the nostril of a patient. The shorter stub tube 11 is intended to have the end of a flexible tube fitted thereover (shown only in dotted lines 16), the flexible tube leading from the output of a manually rechargeable air reservoir 12 which will be described later.

The flat surface of the nozzle plate 5 is also provided with an aperture 13. When the nozzle plate 5 and spacer plate 4 are assembled together, this aperture 13 is positioned over, and in alignment with, the aperture 9 provided in the spacer plate 4, as shown in FIG. 1, to form the base of a bulk reservoir for powder. The nasal tube 10 is positioned over, and in alignment with, drilling 8*b* of the spacer plate 4. The stub tube 11 is positioned over, and in alignment with, the upper end of the drilling 8*a*. As can be seen from FIG. 2 of the application, when the (rotationally fast) assembly of the spacer plate 4 and nozzle plate 5 is rotated around the axis of the cylindrical hub 7, such that the angled drillings 8*a*, 8*b* are positioned over the recess 3 provided in the top plate 2, a continuous passage, suitable for the flow therethrough of gas, is established. This passage (as one travels in the downstream direction) constitutes the bore of stub pipe 11, the bore of angled drilling 8*a*, the generally cup-shaped interior of recess 3, the bore of angled drilling 8*b* and finally the bore of nozzle tube 10. By routing the assembly of the spacer plate and nozzle plate 5, around the longitudinal axis of cylindrical hub 7, in a clockwise direction from the position shown in FIGS. 1-4, the drilling 8*a*, 8*b* are moved out of communication with the recess 3. Instead, the base of the bulk reservoir constituted by aligned apertures 9, 13, is moved into a position above, and in communication with, the recess 3.

By starting with the assembly of the nozzle plate 5 and spacer plate 4 in the position shown in FIGS. 1-4, if the bulk drug reservoir formed by the aligned apertures 9, 13 is filled with powder, for example a physiologically active agent in powdered form, and the assembly 4,5 is then indexed by being rotated 90° clockwise from the position shown in FIGS. 14, when the reservoir is moved into alignment above the recess 3 the powder in the reservoir will no longer be supported by the upper face of the top plate 2, such that powder will fall into the recess 3 to fill it. By then indexing the assembly 4,5 back to the position shown in FIGS. 1-4, by rotating it 90° in an anti-clockwise direction, the excess powder in the reservoir is transported away tom the recess 3 and the powder in the receptacle 3 is scribed off flat by the edge at the base of aperture 9, to leave the recess 3 filled with a volume of powder equal to the internal volume of the recess 3. This volume of powder is known as a metered dose and by varying the volume of the recess 3 the size of the metered dose can obviously be changed. Because the bases of the angled drillings 8*a*, 8*b* are now positioned above the powder-filled recess 3, it will be apparent that if gas is blown vigorously down an upstream gas supply passage formed by the aligned bores of stub pipe 11 and drilling 8*a*, the metered dose of powder in the recess 3 will be displaced from the recess 3 and entrained in the gas as the gas passes along a downstream powder delivery passage constituted by the bores of drilling 8*b* and nasal tube 10.

Once the metered dose has been delivered from the device in the manner described above, by repeating the process of indexing the assembly of the nozzle plate 5 and spacer plate 4 by rotating it through 90° clockwise and then re-indexing it through 90° anti-clockwise, it will be apparent that a fresh dose of powder from the bulk reservoir can be metered in the recess 3 so as to enable the device to be used to deliver a second dose, thus enabling the device to be used to deliver multiple sequential metered doses.

As will become apparent from the later embodiments, the bulk reservoir is likely to be both larger and sealed. In the bench prototype of the embodiment of FIGS. 1-14, the bulk reservoir formed by aligned apertures 9, 13 is very small (and unsealed) and can contain only a very small number of doses of powder.

It will be apparent from the above that the powder metering unit formed by the top plate 2, spacer plate 4 and nozzle plate 5 can be used to meter accurately metered doses of powder from a bulk reservoir containing sufficient loose powder to make up multiple doses of powder.

In this first embodiment, all of the frame 1, top plate 2, spacer plate 4 and nozzle plate 5 are made of metal, for example steel or aluminum. In commercial embodiments it is anticipated that as many of these parts as possible will be made in plastics material, for reasons of both economy and light weight, such a material being well suited to moulding.

In the embodiment of FIGS. 1-14, the forced flow of gas used to discharge the metered dose of powder from the nasal tube 10 is provided by a manually rechargeable air reservoir 12 in the form of a bellows. The bellows is expandable and contractible as denoted by the double-headed arrow 13 in FIG. 2. The bellows is provided with a one way valve on its body, as indicated schematically at 14, as is the air exit 15 from the bellows. Consequently, in expanding the bellows, air enters the bellows via one way valve 14 (and not via bellows exit 15), whereas upon compression of the bellows air is forced from the bellows exit 15 (and not from valve 14).

For reasons of clarity, the flexible pipe 16 which would link the bellows exit 15 to the stub pipe 11 on the nozzle plate 5 has been represented schematically by a pair of dotted lines. The purpose of this flexible pipe is to channel the forced flow of air from the bellows 12 into the bore of the stub pipe 11, for use in entraining and discharging a metered dose of powder.

The bellows 12 is expanded against the restoring bias of a compression spring 17. In the FIG. 1-14 embodiment, the bias of this spring can be modified by changing the position of a plunger 18, relative to a sidewall of the frame 1, but this is not envisaged as being necessary in a commercial device. Once the bellows 12 has been expanded and air drawn into the bellows via the one way valve 14, apart of the spring post 19 provided at the left hand end of compression spring 17 (as drawn in FIG. 2) slides under the end of a resilient spring latch 20. In the condition illustrated in FIG. 2, the bellows 12 is in an expanded position, with the spring 17 compressed, i.e. the air reservoir is primed. Consequently, when the left band end of the spring latch 20 is raised, the spring post 19 is no longer restrained by the spring latch 20, enabling the restoring force of the spring 17 to contract the bellows 12, forcing air out of the bellows exit 15, along the interior of flexible pipe 16, into the bore of stub pipe 11, enabling a metered dose of powder in the recess 3 to be entrained in the air and discharged from the nozzle tube 10.

It will be noted that the bellows 12 is not manually compressed by the user of the device; it is manually expanded. If the bellows were to be manually compressed, the velocity of the gas exiting the bellows exit 15 would be dependent upon the rate of compression of the bellows 12 by the user. Because the rate of gas exit from the bellows exit 15 can influence the way in which the powder of the metered dose is entrained and discharged, it is advantageous to be able to remove this variable from influence by the device user. Consequently, in the illustrated embodiment it is advantageous that all the user has to do, once the bellows 12 is primed (as shown in FIG. 2), is to trigger compression of the bellows 12 by raising the spring latch 20. The rate of compression of the bellows 12 is then determined by the bias of the spring 17.

FIGS. 15-18 illustrate an alternative triggering mechanism for a bellows. For reasons of clarity the surrounding to the mechanism are omitted. For example, it will be appreciated that in this arrangement, the spring 20 used to compress the bellows 21 will need to be braced against some other part of the device.

Figure 15:
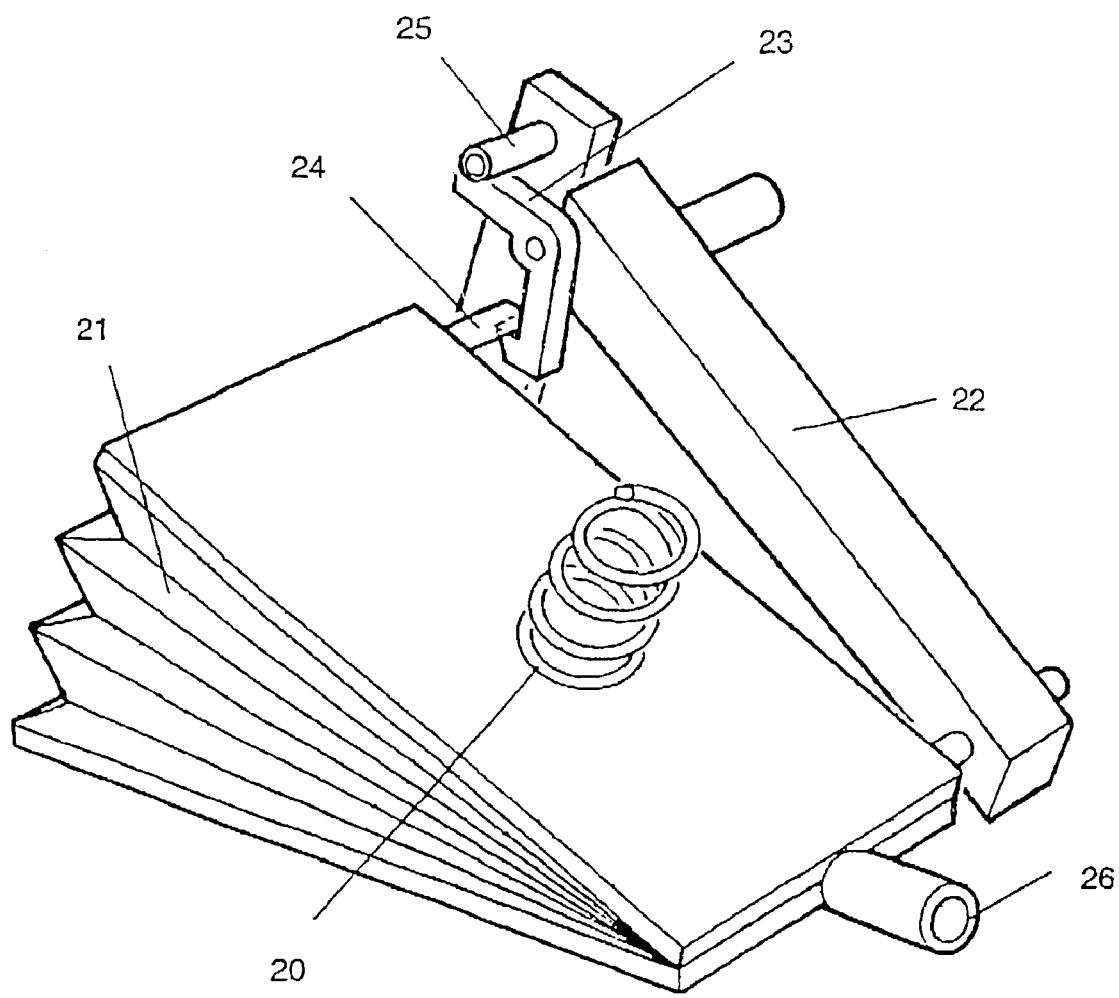
FIG. 15 illustrates an alternative triggering mechanism for the bellows of the first embodiment of device.
Figure 16:
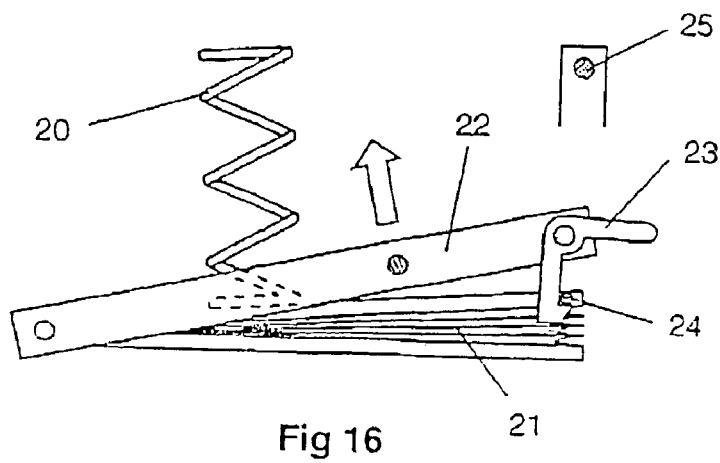
FIGS. 16-18 illustrate a sequence of operation for the alternative triggering mechanism of FIG. 15.
Figure 17:
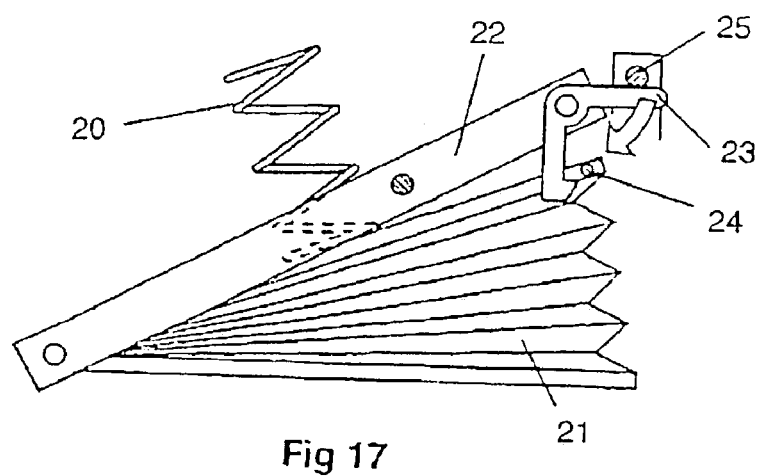
Figure 18:
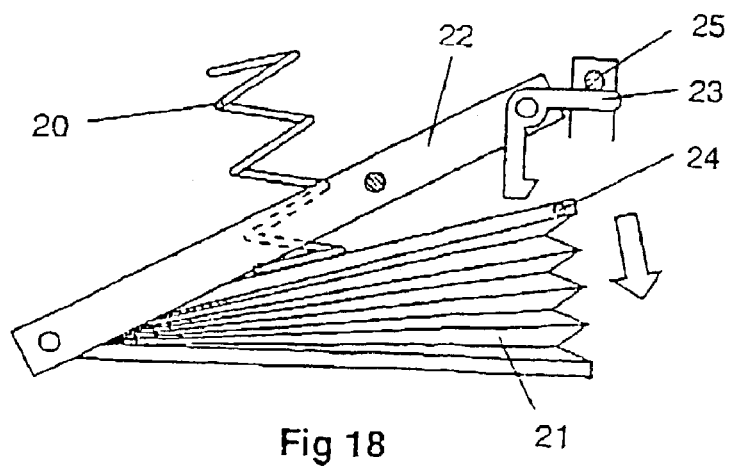

In the FIG. 15-18 arrangement, an operating lever 22 is provided. At one end of the operating lever 22 the lever is hinged adjacent the bellows air exit 23. At the other end a latch 23 is pivotally attached to the lever 22. Upon lifting the latch end of the lever 22, engagement of the latch 23 with a pin 24 provided on one of the side walls of the bellows 21 causes the bellows to be expanded, as shown in FIGS. 15 and 16. When the bellows 21 have been fully recharged with air, the latch 23 engages the underside of a stop peg 25, such that continued liking movement of the lever 22 causes the stop peg 25 to pivot the latch 23 around its point of attachment to the lever 22, moving the hook provided at the base of the latch 23 free from engagement with the pin 24 (as shown in FIG. 17). This enables the sprint 20 to compress the bellows (as shown in FIG. 18) to force air out of the bellows exit 23. In this arrangement it will be appreciated that the bellows may be recharged with air, and then have its release triggered, all using one lever. For example, in the case of the device being used to deliver powder to the nasal cavity of a patient, once the nasal tube is inserted in the patient's nostril the patient could in one simple movement of the lever 22 both recharge the bellows with air and then release that charge of air, avoiding the need to have one lever or control for priming the rechargeable air reservoir and another control element for triggering release of air from the primed air reservoir.

Figure 19:
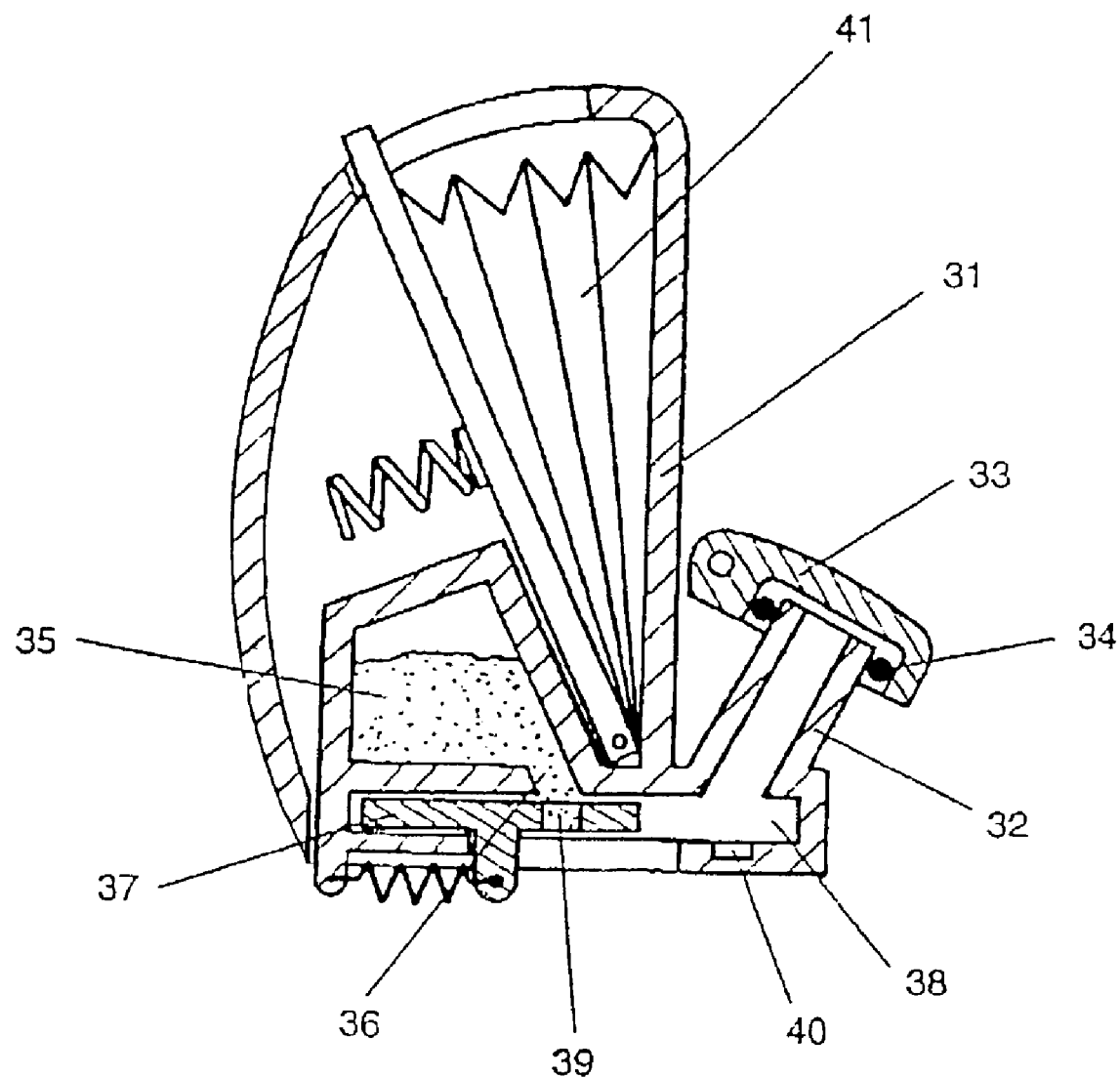
FIG. 19 illustrates a second embodiment of device for delivering multiple doses of physiologically active agent in powdered form, in cross-sectional side elevation.

FIG. 19 illustrates a second embodiment of device for delivering multiple doses of physiologically active agent in powdered form. The device is intended to be hand-held and comprises a main body which may advantageously be moulded in plastics material as may most of the components of the device in this and the other embodiments.

In the second embodiment the main body 31 includes a nasal tube 32 for insertion in the nostril of a patient and defining internally a powder delivery passage. To restrict the unwanted ingress of airborne moisture into the device through the powder delivery passage, the distal or downstream end of the nasal tube 32 is provided with a closure 33 in the form of a hinged lid. The lid to tube seal may, as shown, be enhanced by the provision of an O-ring 34. In addition to inhibiting the inflow of moisture into the device, which could adversely affect the powdered agent, the closure 33 also has the advantage of preventing debris from entering the device via the powder delivery passage.

In the second embodiment the bulk reservoir 35 containing multiple doses of powder has an aperture or exit 36 provided in its base surface. A powder metering slide 37 is positioned below the bulk reservoir 35 and is intended to slide linearly (horizontally as drawn) in a guide channel 38. The drug metering slide 37 is provided with a recess in the form of a through aperture 39 which through sliding movement of the slide 37, can be moved from alignment with the bulk reservoir exit 36 (as shown in FIG. 19) to be aligned, instead, with the powder delivery passage provided in the nasal tube 32. When the powder metering slide 37 is in the position shown in FIG. 19, powder from the bulk reservoir 35 will, under the influence of gravity, enter and fill the aperture 39 provided in the slide 37. The bottom interior surface of the guide channel 33 will fit closely against the bottom surface of the slide 37, such that powder will not fall out of the bottom of the aperture 39. By then moving the slide 37 to the right (as drawn) the aperture 39 may be transported into alignment with the powder delivery passage provided in the nasal tube 32, and with a passage 40 opening out of the base of the channel 38, which passage 40, in use, forms the upstream air supply passage (from the bellows 41). In moving to the right (from the position shown in FIG. 19), the top surface of the slide 37, to the left of the aperture 39, slides underneath the aperture 36 provided in the base of the bulk reservoir 35 to prevent powdered drug from falling out of the reservoir aperture 36 to foul the channel 38. It will be appreciated that the recess 39 formed in the slide form a cup for meters out the required dose of powder.

Once the metered dose in the aperture 39 of the slide 37 has been moved into alignment with the downstream powder delivery passage, it will be appreciated that, by operating the bellows 41 to discharge therefrom a charge of air, the forced flow of air from the bellows 41 to the upstream air supply passage 40 (only the downstream end of which is visible in FIG. 19) will displace the metered dose of powder from the aperture 39 and entrain it in the forced air flow prior to exiting from the distal end of the nasal tube 32 past the opened closure 33.

The arrangement for priming and triggering the bellows 41 in the second embodiment may be as in the first embodiment of FIGS. 1-14, or may alternatively be as described above in connection with FIGS. 15-18.

In the second embodiment the drug metering slide 37 is manually indexed by the user from the position shown to bring its aperture 39 into alignment with the downstream powder delivery passage, prior to the forced flow through the aperture 39 of air from the bellows 41. Once the device has been used to deliver a metered dose of powder, the slide 37 will need to be moved back to the left, to meter out a fresh dose of powder, prior to being moved back to the right in order for the device to be used to deliver a subsequent dose.

The third embodiment of device, described below in conjunction with FIG. 20, avoids the need to have a separate manual action to index the drug metering slide, by liking this indexing movement with another task which the device user has to perform, namely movement of the closure covering the nasal tube.

Figure 20:
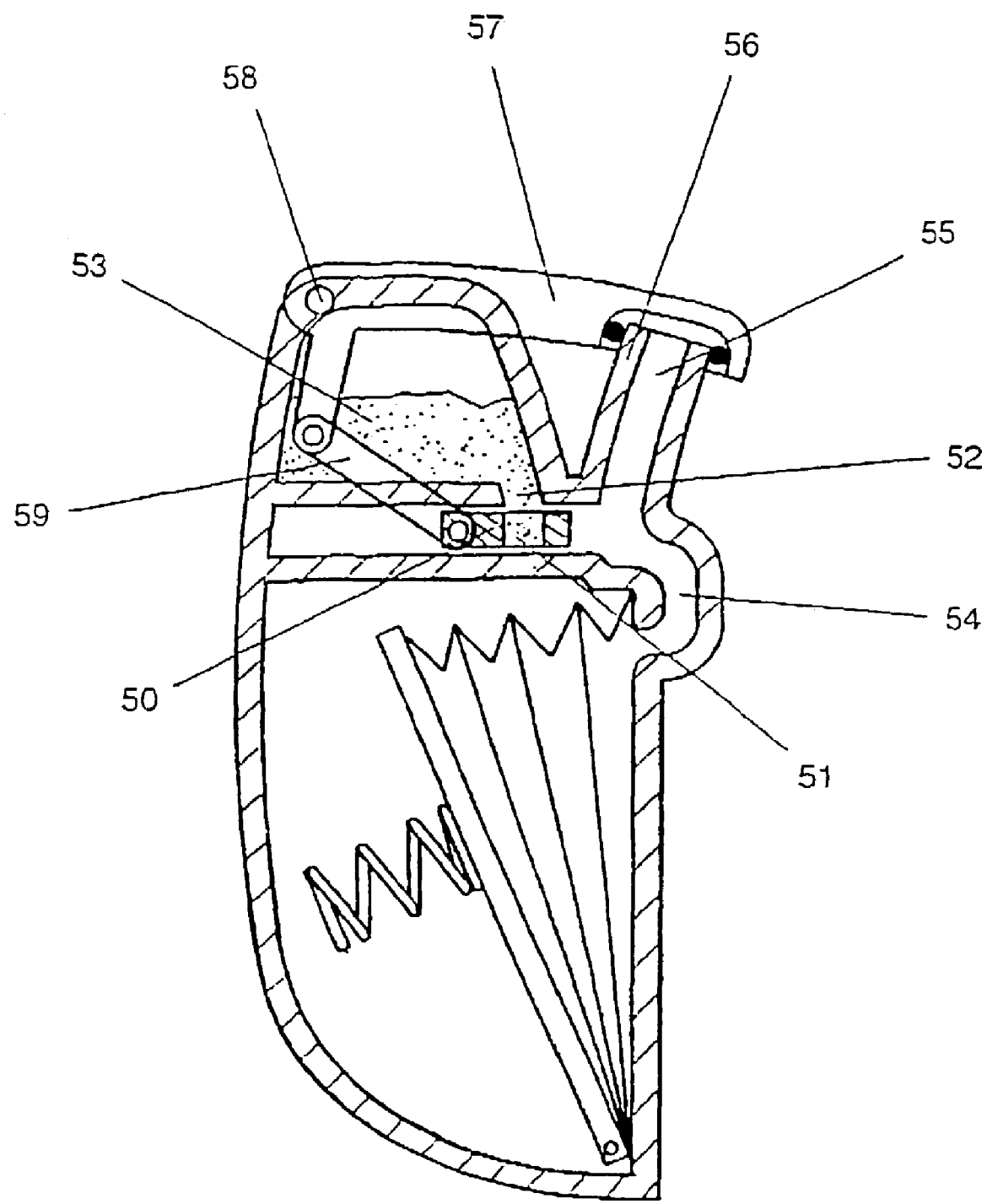
FIG. 20 illustrates a third embodiment of device for delivering multiple doses of physiologically active agent in powdered form, in cross-sectional side elevation.

In the third embodiment of device, illustrated in FIG. 20, although the layout of the main components (bulk reservoir, bellows and nasal tube) is different from that in the second embodiment (see FIG. 19), the principle of operation of the device is fundamentally similar in that a powder metering slide 50 is provided which is movable linearly from having its powder receiving aperture or recess 51 aligned with the exit 52 from its bulk reservoir 53 to a position (to the right as drawn in FIG. 20) in which the metering slide's aperture 51 is positioned in line with an upstream air supply passage 54 (leading from the bellows exit) and a downstream powder delivery passage 55 formed by the nasal tube 56.

The main difference between the second and third embodiments resides in the manner in which the powder metering slide 50 is moved between its two main positions. As can be seen, the closure 57, which closes the nasal tube 56 when the device is not in use, is attached to the main body of the device at a hinge point 58. The closure is, however, additionally connected to the drug metering glide 50 via a linkage 59. As the closure 57 is opened prior to using the device, in pivoting anti-clockwise (as drawn) around its hinge point 58, the linkage 59 acts as a pushrod to slide the powder metering slide 50 to the right from the position shown in FIG. 20. When the closure 57 is fully opened, the drug metering slide 50 will have been moved sufficiently far to the right that its aperture 51 will then be coaxially aligned with the upstream air supply passage 54 and the downstream powder delivery passage 55, making the device ready for use.

Once the device is readied for use in this way, a charge of gas can be released from the bellows. The forced flow of air up the upstream air supply passage 54 will displace the metered dose of powder from the aperture 51 in the drug metering slide 50 and the powder, entrained in the air flow, will exit the device via the downstream powder delivery passage 55. If, when the device is used, the distal end of the nasal tube has been inserted into the nostril of a patient, it will be appreciated that in this way the metered dose of powder can be delivered to the nasal cavity of the patient. In the FIG. 20 device, the arrangement and operation of the bellows may be as described in conjunction with any of the earlier Figures.

It will be appreciated that the above described third embodiment of device should be simpler to use than the second embodiment of device in that it avoids the need for the device user to consciously index the powder metering slide manually. By linking the indexing movement of the metering slide with a task which the user cannot avoid performing prior to using the device, namely opening the closure, the number of discrete tasks which the device user has knowingly to perform prior to using the device is reduced.

It will be noted that the embodiments described so far, and the subsequent embodiment, all rely on the forced flow of gas, from upstream of the metered dose, to displace and entrain the powder. The patient is not required to inhale, although inhalation can be taking place at the moment of powder release. This applies whether the device is used to deliver powder to the nasal cavity of a patient or is used in pulmonary powder delivery via the patient's mouth. In this way, another potential variable is eliminated. In the case of a nasal powder delivery device, different patients can "sniff" with different levels of vigour, affecting the efficiency of powder/air entrainment and powder delivery. Additionally, if a patient has a cold, or is otherwise suffering from a stuffy nose, making it difficult to inhale through the nose, in the absence of a forced gas delivery from within the device, the powder of the powder delivery would risk being adversely affected.

Figure 21:
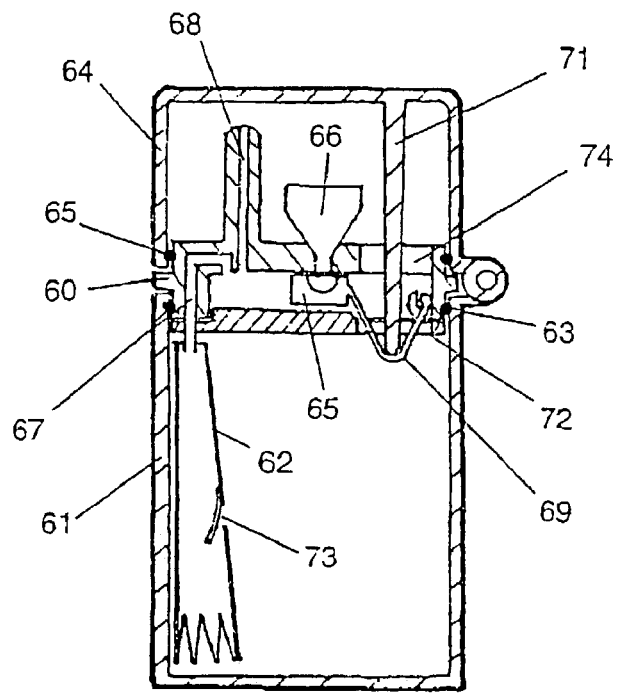
FIGS. 21 and 22 illustrate, in cross-sectional side elevation, a fourth embodiment of device for delivering multiple doses of physiologically active agent in powdered form, FIG. 21 showing the device's closure closed and FIG. 22 showing the closure opened.
Figure 22:
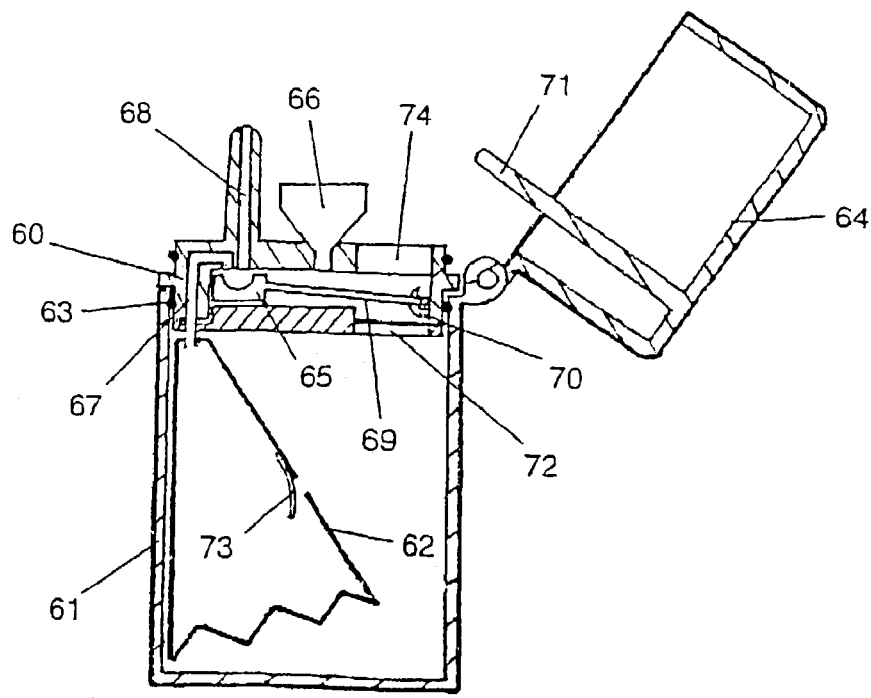

FIGS. 21 and 22 illustrate a fourth embodiment of device. This device works on a similar principle to the previous devices.

The fourth embodiment of device comprises a main element 60 incorporating the powder metering unit. A base housing 61, enclosing the bellows 62, seals against the main element 60, this seal being enhanced by the provision of an O-ring seal 63. A closure 64, in the form of a hinged cover, is attached to the base housing 61 by a hinge. To enhance sealing of the closure 64 to the main element 60 a further O-ring 65 is provided.

In common with the second and third embodiments, in the fourth embodiment the powder metering unit includes a metering slide 65. Unlike in the second ad third embodiments, the recess provided in the slide for receiving the metered dose of powder comprises a U-shaped cup, opening only into the top face of the slide, such that the forced air flow to dislodge the metered dose of powder both enters and exits the powder-containing recess through the single aperture in the top face of the slide 65. The absence of a through hole in the slide 65 eliminates the possibility of particles falling downwardly through a hole in the slide, which is a possibility with the second and third embodiments described above.

As in the second and third embodiments, the metering slide 65 is movable between two main positions.

The first position is one in which the recess in the metering slide can receive powder from the bulk reservoir 66, in which position it is isolated from both the upstream air supply passage 67 and the downstream powder delivery passage 68. This first position is shown in FIG. 21.

The second main position for the metering slide is shown in FIG. 22. In the second position, displaced from the first position, the recess in the metering slide is coincident with both the upstream air supply passage 67 and the downstream powder delivery passage 68 and is isolated from the bulk reservoir 66. In common with the second and third embodiments, in the fourth embodiment it is the action of the powder-containing recess formed in the metering slide moving out of alignment with the powder exit from the bulk reservoir 66 which controls the amount of powder in the metered dose.

As in the third embodiment, the fourth embodiment is constructed and arranged so that the metering unit is operated by the action of moving the closure 64. In the fourth embodiment of FIGS. 21 and 22, the metering slide is provided with a flexible linkage 69 which is pivotally attached to a hook 70 at the right hand end of the channel in which the slide moves. The flexible linkage 69 is sufficiently stiff and resilient, for example being made of plastics material, that when not acted upon by external influences it will straighten (as shown in FIG. 22), causing the metering slide to move to the aforementioned second position. When the closure 64 is closed, a downwardly depending element 71 contacts the flexible linkage 69 to deflect it laterally through aperture 72, drawing the metering glide 65 to the right, such that when the closure 64 is fully closed the slide 65 is in the aforementioned first position.

It will thus be appreciated that when, prior to using the device to discharge powdered drug, the closure 64 is opened, the metering slide will move automatically from its fast position to its second position, to carry a metered dose of powder into alignment with the air supply and powder delivery passages, 67,68. In this condition, the forced flow of gas from the manually rechargeable air reservoir, in the form of bellows 62, will deliver the powder in the manner discussed above.

Once the charge of air has been released from the bellows 62 to discharge the metered dose of powder from the recess of the slide 65 to the nostril of a patient via the downstream powder delivery passage 68, the action of the patient closing the closure 64 will cause the slide 65 to be moved back from its second position to its first position to receive a fresh metered dose of powder. This fresh metered dose will stay in the recess of the slide 65 until such time as the device is next required to be used to discharge a metered dose of powder, whereupon re-opening of the closure 64 will cause the above tax of events to commence again.

With many powdered physiologically active agents, moisture can have an adverse effect. For example, moisture ingress into the device can adversely affect the delivered dose of agent by coating surfaces and causing agglomeration of the powder. The design of the fourth embodiment of device is effective in restricting the unwanted ingress off air (and thus moisture) into the device when the device is not in use.

In order for the bellows 62 to be able to intake air through one way valve 73 upon recharging of the air reservoir, air must be capable of entering the base housing 61 when the bellows are being expanded. In the fourth embodiment of the device, when the closure 64 is opened, air can enter the base housing 61 through the above-mentioned aperture 72 and a further aligned aperture 74 provided in the main element 60. This entry of air is denoted by the arrow 75 in FIG. 22. When the device is not being used, the closure 64 is closed (as in FIG. 21). Not only does the closure 64 prevent the unwanted ingress of ambient air (and moisture) through the powder delivery passage in the nasal tube, but it also has the effect of sealing the apertures 72,74 such that the maximum amount of moisture that can be present in the device will be that present in the device, and the air trapped in the device, at the tune the closure 64 is closed after use.

Although the closure 64 is shown as being hinged to the remainder of the device, it will be appreciated that the closure 64 could equally well be completely detachable from the remainder of the device, such that to open the closure one removes it from the remainder of the device and replaces it after use. The hinged arrangement in FIGS. 21 and 22 is preferred because it prevents the closure 64 from being detached and getting lost.

Although, in one cycle of opening and closing the closure 64, the powder metering slide 65 moves from its first position to its second position (on opening) and from its second position back to its first position (on closing), other movement possibilities are envisaged. For example, upon opening the closure, the metering slide 65 might start at its second position, move initially to its first position (to receive a metered dose of powder) and then move back to the second position. Alternatively, there might be a third position for the metering slide, in which the powder-containing recess in the slide is neither capable of receiving powder from the bulk reservoir 66 nor coincident with either of the air supply passage 67 or the powder delivery passage 68, and from which, when the closure 64 is opened, the slide 65 is moved to the first position and then to the second position.

In a yet further variation, the metering slide 65 might be moved to its first position by the action of opening the closure, although in this case some means would need to be provided to move the slide subsequently to its second position prior to activation of the device to discharge the powder.

In the device illustrated in FIGS. 21 and 22, the bellows 62 may take the form of any of the bellows described above, with regard to charging and/or triggering release of a charge of air. Alternatively, rather than having a mechanism for priming the bellows 62, requiring a dedicated priming action to be performed by the user, priming of the bellows could advantageously be linked to another operation which the user of the device already has to perform. For example, priming of the bellows might also be linked to the action of opening or closing the closure 64. Although no such mechanism for this is shown in FIGS. 21 and 22, in a manner similar to that in which the metering slide 65 is indexed by opening and closing the closure 64, the bellows 62 might also be primed (i.e. expanded to recharge with air) upon opening or closing the closure 64. As an example, one could utilise the action of opening the closure 64 both to move the metering slide 65 from its first position to its second position and to expand the bellows. Whilst a separate trigger could be provided for triggering release of the primed bellows when the patient wishes to use the device to discharge powder, in a further refinement of the above-mentioned idea triggering of the release of the bellows could also be linked to movement of the closure 64. For example, part of the full range of movement of the closure 64 might be used to move the metering slide 65 to its second position and to charge the bellows 62, with the final portion of the closure's range of movement being used to trigger release of the bellows, i.e. to "fire" the device.

Figure 23:
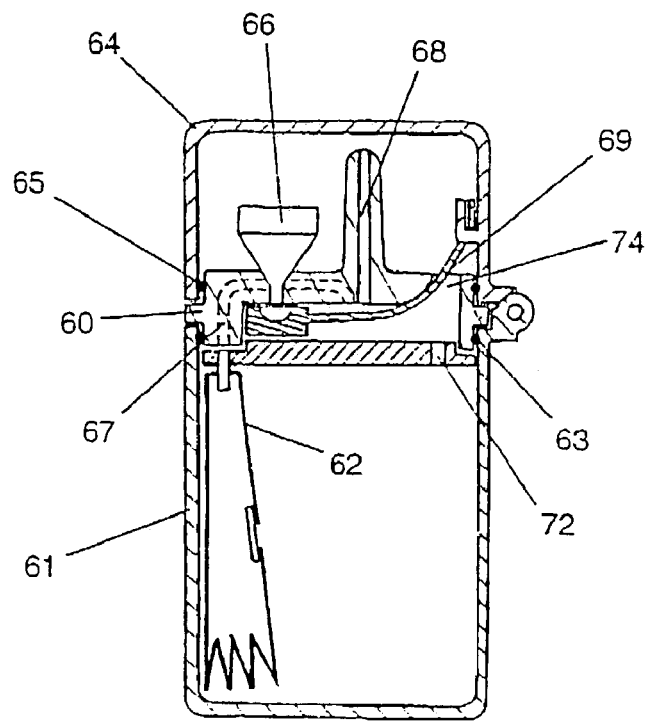
FIGS. 23 and 24 illustrate, in cross-sectional side elevation, a fifth embodiment of device for delivering multiple doses of physiologically active agent in powdered form, FIG. 23 showing the device's closure closed and FIG. 24 showing the closure opened.
Figure 24:
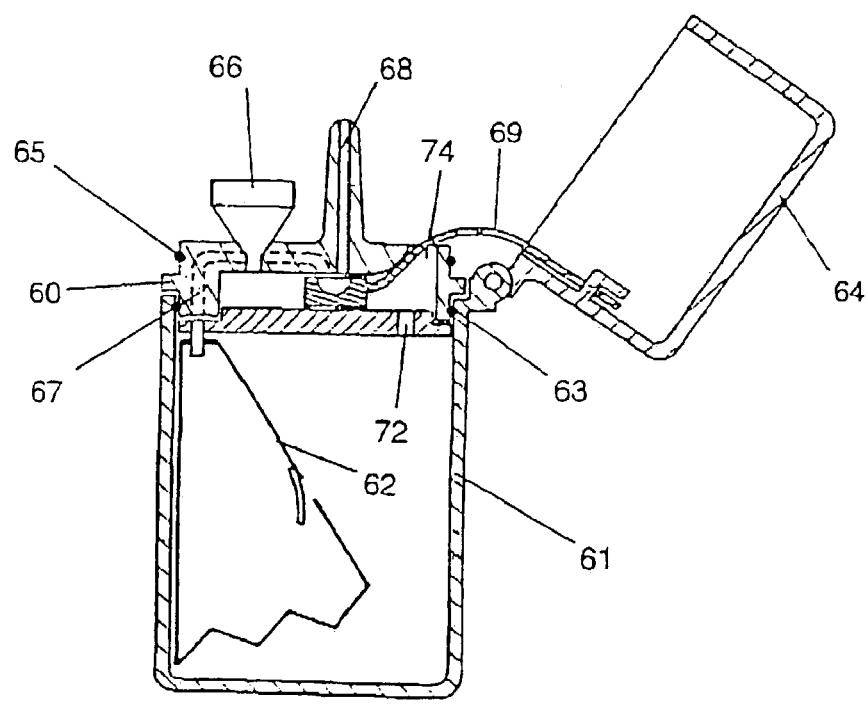

The fifth embodiment illustrated in FIGS. 23 and 24 of the application is fundamentally similar to that of the fourth embodiment of FIGS. 21 and 22. In FIGS. 23 and 24 similar parts have been given the same reference numerals as in FIGS. 21 and 22. The main difference, apart from a slight change in general layout, is in the agreement of the linkage 69.

In the fifth embodiment of FIGS. 23 and 24, the right hand end of the linkage 69 is attached to the closure 64, rather than to a hook 70 provided at the stationary right hand side of the main element 60. In this way, the need to have a downwardly depending element 71 to displace the linkage 69 laterally can be avoided.

The sixth and seventh embodiments of device illustrated in FIGS. 25-29 of the application are fundamentally different to the earlier embodiments in that they do not employ a bulk reservoir for containing multiple doses of powder and do not meter out doses of powder from that bulk reservoir within the device. Instead, each of the devices is provided with a powder container defining therein a plurality of individual receptacles, each receptacle containing a discrete metered dose of powder. This avoids the need for a dose of powder to be metered within the device; instead, the doses can be pre-metered in a factory before the powder container is associated with the remainder of the device.

Figure 25:
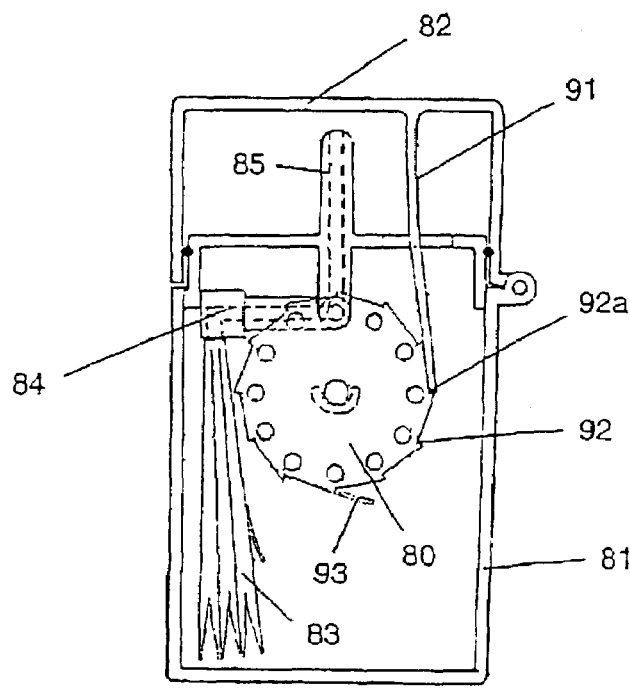
FIGS. 25 and 26 illustrate, in cross-sectional side elevation, a sixth embodiment of device for delivering multiple doses of physiologically active agent in powdered form, FIG. 25 showing the device's closure closed and FIG. 26 showing the closure opened.
Figure 26:
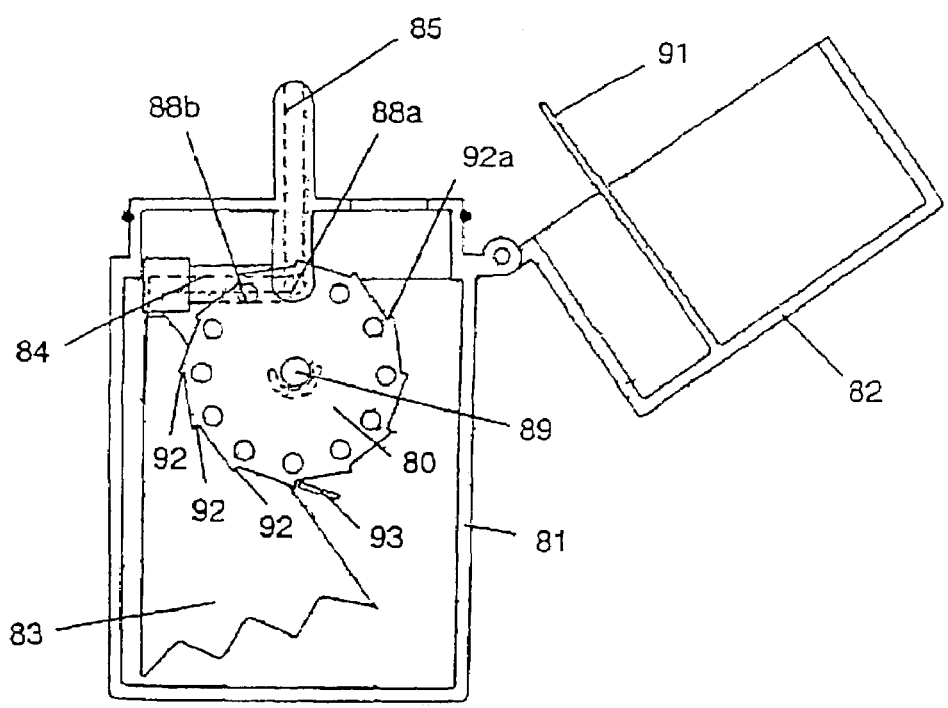
Figure 27:
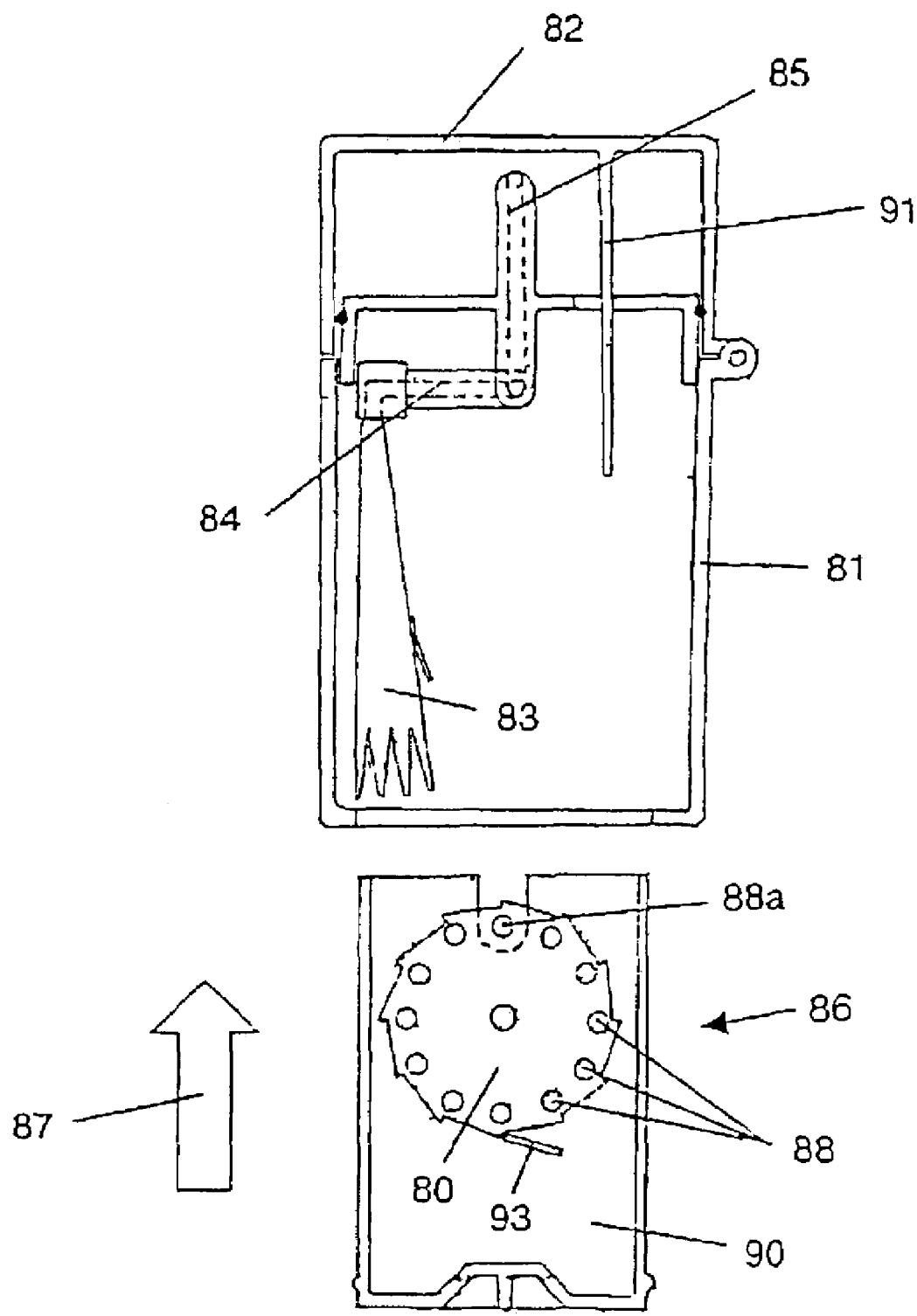
FIG. 27 is a similar view to that of FIG. 25, but showing a cassette housing the powder container removed from the remainder of the sixth embodiment of device.

In the sixth embodiment of device illustrated in FIGS. 25-27, the device comprises a base housing 81 having an openable closure 82 attached thereto by a hinge.

A bellows 83 is provided in the base housing and feeds into the upstream end of an upstream air supply passage 84. This air supply passage terminates at a downstream end that is aligned with but spaced apart from, the upstream end of a downstream drug delivery passage 85. This spacing is equivalent to the axial thickness of the powder container 80, such that when a removable cassette 86 housing the powder container 80 is slid (in the direction of arrow 87 in FIG. 27) into the open bottom of the base housing 81, a circumferential portion of the rotatable powder container 80 will be snugly received in the gap between the downstream end of the upstream air supply passage 94 and the upstream end of the downstream drug delivery passage 85.

It should be noted that, for reasons of clarity, the structure of the removable cassette 86 has been omitted from FIGS. 25 and 26, although the powder container 80 has been shown in FIGS. 25 and 26.

The powder container 80 is provided in the region of its circumference with twelve receptacles 80 in the form of throughbores. Each of these throughbores 80 is sized to contain a discrete pre-metered dose of powder for delivery. The powder container 80 is mounted on a spindle 89 to allow it to be rotatably indexed, as will be described below. In the position shown in FIG. 27, only the open first and second opposite ends of the uppermost throughbore 88a are exposed. The opposite ends of the remaining eleven throughbores are closed by the main walls 90 of the removable cassette 86, only one of these walls 90 being visible in FIG. 27. Consequently, the metered doses of powder contained within these eleven closed throughbores are presented from leaking out of the throughbores—any leakage would be undesirable as it could lead to under dosing.

It ill be appreciated that when the removable cassette 86 is slid fully into position in the direction of arrow 87, the uppermost throughbore 88a will become axially aligned with the downstream end of the upstream air supply passage 84 and the upstream end of the downstream drug delivery passage 85. Consequently, when the bellows 83 is released from the condition shown in FIG. 26, a charge of air will be forced through the upstream air supply passage 84 to displace the dose of powder from the aligned receptacle 88a and the resultant displaced powder will be entrained in that air and expelled from the downstream end of the downstream drug delivery passage 85.

Following such a dosing event, it is anticipated that the closure 82 will be hinged shut (from the FIG. 26 position) to attain the position shown in FIG. 25. In being hinged shut, a flexible indexing finger 91 will move into contact with one of the twelve gear teeth 92 provided around the periphery of the powder contester 80. In particular, the tip of the flexible indexing finger 91 will come into contact with the gear tooth 92a in the 2 o'clock position (as drawn in FIG. 26). Continued closing of the closure 82 after this finger-to-tooth contact is established will rotate the powder container 80 through $\frac{1}{12}$ of a turn in the clockwise direction, such that the gear tooth 92a ends up in the 3 o'clock position, as shown in FIG. 25, and will flex the finger 91 slightly sideways. In so doing, it will be appreciated that the throughole 88b which was previously in the 11 o'clock position as drawn in FIG. 26 will be rotated into the position, between the upstream air supply passage 84 and the downstream drug delivery passage 85, previously occupied by throughole 88a. In this way, the receptacle empty of powder (throughole 88a) will be moved out of communication with the passages 84, 85. Instead, a fresh receptacle (88b) containing a fresh metered dose of powder will be moved into communication with those two passages 84,85, so that when the closure 82 is next opened in preparation for a dosing event a fresh dose of powder will be capable of being discharged.

To prevent unwanted rotational movement of the powder container 80 in the removable cassette 86 a pawl 93 is provided to cooperate with the gear teeth 92 of the ratchet-like container 80.

The mechanisms for priming the bellows 83 and triggering "firing" of the bellows 83 in the sixth embodiment has been omitted so as to improve clarity; these could be as in one of the previously described embodiments.

Advantageously, the powder container 80, as well as the body of the removable cassette 86, the base housing 81 and the closure 82 are injection moulded in an engineering plastics material.

Once twelve dosing events have taken place, all of the individual powder-containing receptacles 88 in the powder container 80 will have become exhausted. In this situation, the cassette 86 can be removed from the device by pulling on the integrally moulded handle 94 and the removed cassette 86 discarded. In its place, an entirely fresh replacement cassette 86 can be inserted, to enable the device to be used for a further twelve dosing events.

It will be appreciated that the powder container could be provided with greater or fewer powder-containing receptacles.

Figure 28:
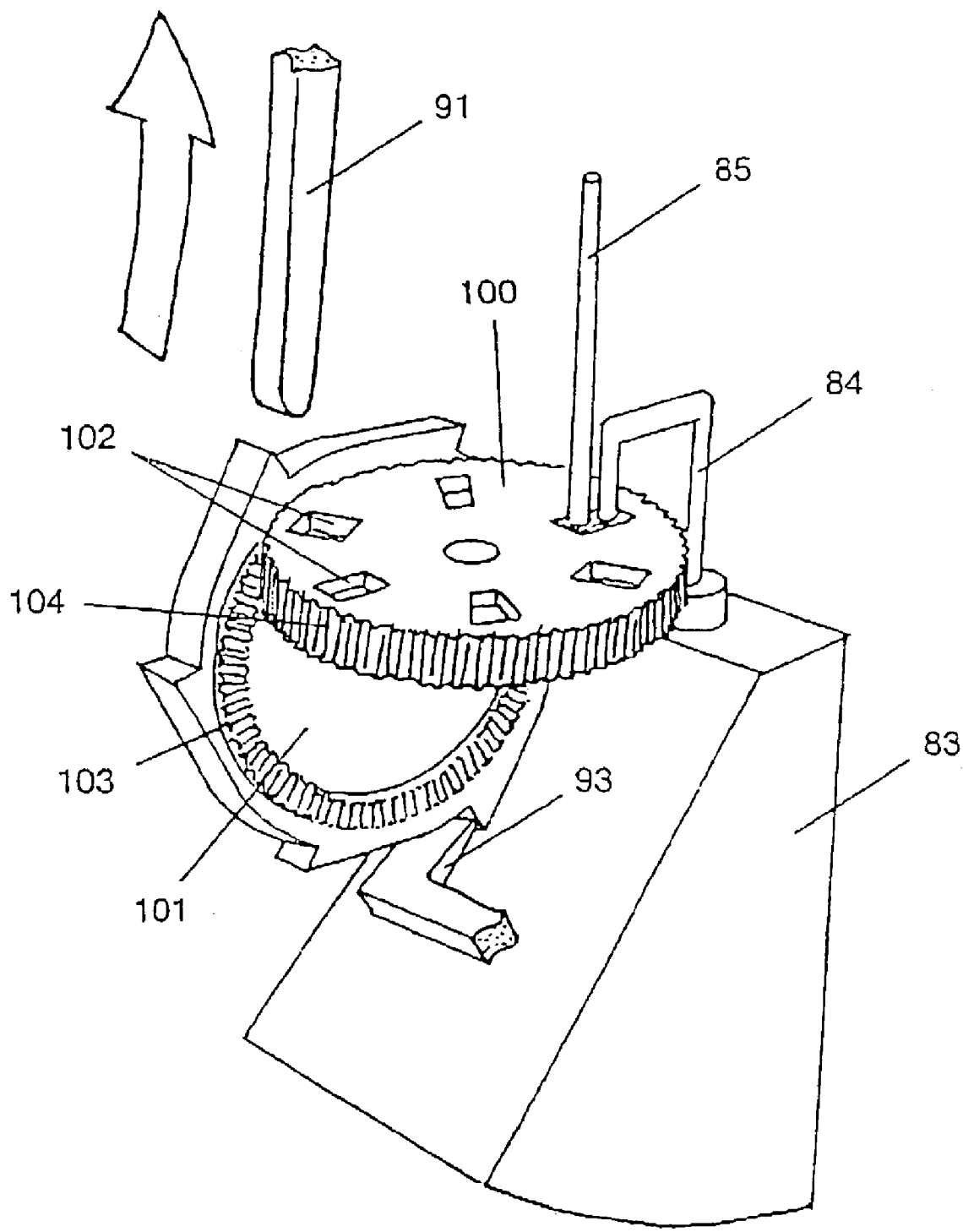
FIGS. 28 and 29 are perspective views of a powder containing indexing mechanism suitable for use in a seventh embodiment of device for delivering multiple doses of physiologically active agent in powdered form.
Figure 29:
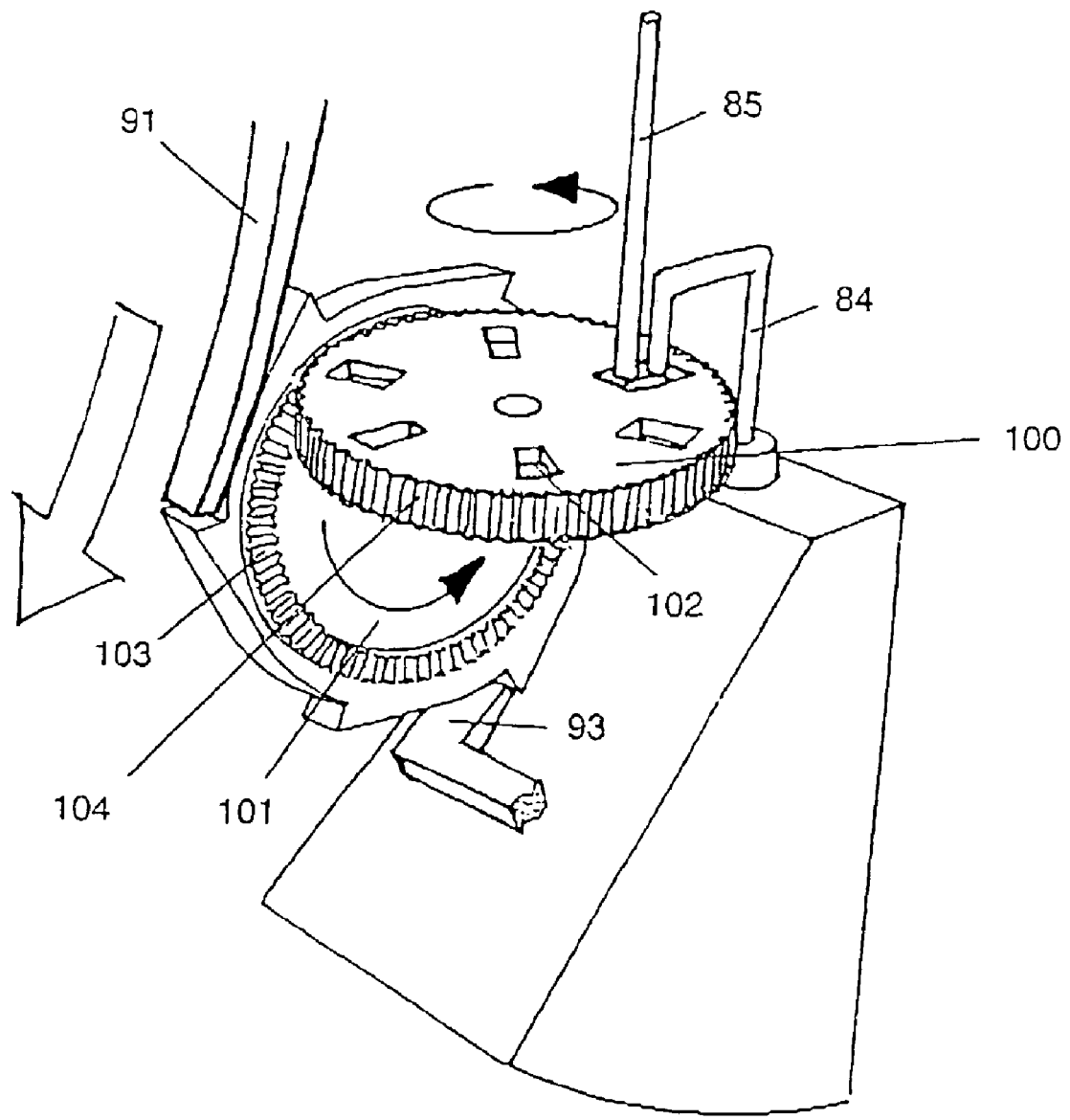

Although in FIGS. 25-27 the powder container 80 is acted on directly by the flexible indexing finger 91, this need not be so. For example, as shown in FIGS. 28 and 29, a separate gear wheel can be provided between the flexible indexing finger 91 and the powder container 100. In the FIG. 28 and 29 arrangement, a gear wheel 101 is provided with its number of gear teeth matching the number of powder-containing receptacles provided in the powder container 100, this number being six in the illustrated arrangement. By providing one face of the gear wheel 101 with a circular track of teeth 103, which teeth are meshed with teeth 104 provided around the periphery of the powder container 100, rotational movement of the gear wheel 101 in the vertical plane can be translated into rotational movement of the drug container 100 in the horizontal plane.

A further difference between the arrangement illustrated in FIGS. 28 and 29, that when the closure 82 is next opened in preparation for a dosing event a fresh dose of powder will be capable of being discharged.

To prevent unwanted rotational movement of the powder container 80 in the removable cassette 86 a pawl 93 is provided to cooperate with the gear teeth 92 of the ratchet-like container 80.

The mechanisms for priming the bellows 83 and triggering "firing" of the bellows 83 in the sixth embodiment has been omitted so as to improve clarity; these could be as in one of the previously described embodiments.

Advantageously, the powder container 80, as well as the body of the removable cassette 86, the base housing 81 and the closure 82 are injection moulded in an engineering plastics material.

Once twelve dosing events have taken place, all of the individual powder-containing receptacles 88 in the powder container 80 will have become exhausted. In this situation, the cassette 86 can be removed from the device by pulling on the integrally moulded handle 94 and the removed cassette 86 discarded. In its place, an entirely fresh replacement cassette 86 can be inserted, to enable the device to be used for a further twelve dosing events.

It will be appreciated that the powder container could be provided with greater or fewer powder-containing receptacles.

Although in FIGS. 25-27 the powder container 80 is acted on directly by the flexible indexing finger 91, his need not be so. For example, as shown in FIGS. 28 and 29, a separate gear wheel can be provided between the flexible indexing finger 91 and the powder container 100. In the FIGS. 28 and 29 arrangement, a gear wheel 101 is provided with its number of gear teeth matching the number of powder-containing receptacles provided in the powder container 100, this number being six in the illustrated arrangement. By providing one face of the gear wheel 101 with a circular track of teeth 103, which teeth are meshed with teeth 104 provided around the periphery of the powder container 100, rotational movement of the gear wheel 101 in the vertical plane can be translated into rotational movement of the drug container 100 in the horizontal plane.

A further difference between the arrangement illustrated in FIGS. 28 and 29, and that illustrated in FIGS. 25-27, is that in the FIG. 28 and 29 arrangement the powder containing receptacles 102 are not throughbores but are instead cup-shaped. Consequently, only the upper surface of the powder container 100 has openings formed therein and the upstream air supply passage 84 and the downstream drug delivery passage 85 both face into the receptacles 102 (when aligned therewith) through this single, upwardly facing opening.

In FIGS. 23 and 29, many items have been omitted so as to improve clarity. As in the FIGS. 25-27 arrangement, a face plate with a small sector cut away around the downstream end of the upstream air supply passage 84 and the upstream end of the downstream drug delivery passage 85 may be placed over the top of the powder container 100 so that only one powder-containing receptacle 102 is open at any given time.

In the arrangement illustrated in FIGS. 25-29, a foil membrane could be provided over each of the receptacles, which membrane is slit or otherwise ruptured prior to the contents of the respective receptacle being discharged. This would enhance the protection of the doses against degradation from airborne moisture.

In the above described different embodiments, except where features present in one embodiment are incompatible with another embodiment, those features may be interchanged. Consequently, when a feature is described in conjunction with one embodiment for example using the action of opening or closing a closure to recharge the manually rechargeable air reservoir, this facility is applicable to all of the embodiments. Similarly, except where incompatible, the feature or features of each claim should be considered as being disclosed herein as suitable for use in conjunction with the feature or features of every other claim.

Although in the illustrated embodiments the manually rechargeable air reservoir takes the form of an inflatable bellows provided with a spring bias, with the bellows being expanded against the spring bias to charge the bellows with air, these means may alternatively take the form of a cylinder and piston arrangement. In such an arrangement the piston could be provided with a spring bias, with the piston being moved against the spring bias to sweep the cylinder to charge the cylinder with air ready for triggering and air release.

The invention claimed is:

1. A device for delivering multiple doses of physiologically active agent in powdered form, the device comprising:
   a manually rechargeable air reservoir,
   a powder container defining therein a plurality of individual receptacles, each receptacle containing a discrete metered dose of powder,
   a powder delivery passage for the forced flow therealong to a patient of gas with said metered dose of powder entrained therein so as substantially to empty said receptacle,
   a closure for restricting an unwanted ingress of moisture into the device via said passage when the device is not in use, and
   a container indexing mechanism for indexing movement of said container to move a substantially empty receptacle out of communication with said powder delivery passage and to move a fresh powder-containing receptacle into communication with said powder delivery passage,
   wherein the device is constructed and arranged so that an action of opening or closing said closure operates said container indexing mechanism and charges the air reservoir with air.

2. A device as claimed in claim 1, wherein said container indexing mechanism is arranged to perform said indexing movement upon the action of opening said closure in preparation for using the device for powder delivery.

3. A device as claimed in claim 1, wherein the powder container is arranged to revolve around an axis when said indexing movement is performed.

4. A device as claimed in claim 1, further comprising an air supply passage for the forced flow therealong of air from the air reservoir:
   wherein, when said receptacle is in communication with said gas delivery passage that same said receptacle is also in communication with said air supply passage, whereby said forced flow of air along said air supply passage can be used to dislodge the discrete metered dose of powder from the said receptacle and to entrain said dislodged powder in said air for delivery of the entrained powder to the patient via said powder delivery passage.

5. A device as claimed in claim 4, wherein each receptacle provided in said powder container is generally cup-shaped and has a single opening, wherein each receptacle is arranged to communicate with said air supply passage and said powder delivery passage via its said single opening.

6. A device as claimed in claim 4, wherein each receptacle provided in said powder container is a through bore having open first and second opposite ends, wherein each reservoir is arranged to communicate with said air supply passage and said powder delivery passage via its first and second ends respectively, such that in use the forced flow of air passes generally longitudinally through the throughbore.

7. A device as claimed in claim 1, wherein the container indexing mechanism comprises an indexing element arranged to move upon opening or closing of said closure, which element is arranged to index movement of said powder container.

8. A device as claimed in claim 7, wherein the indexing element is arranged to act directly on the powder container to cause said indexing movement.

9. A device as claimed in claim 8, wherein the indexing element comprises a flexible indexing finger, which finger is arranged to contact the periphery of the powder container to cause said indexing movement.

10. A device as claimed in claim 9, wherein the tip of the flexible indexing finger is arranged to contact and push on a gear tooth to convert generally longitudinal motion of the flexible indexing finger into generally rotational movement of said powder container.

11. A device as claimed in claim 10, wherein said gear teeth resemble a ratchet and a pawl is provided to inhibit unwanted movement of said ratchet.

12. A device as claimed in claim 7, wherein the indexing element is arranged to act indirectly on the powder container to cause said indexing movement.

13. A device as claimed in claim 12, wherein the indexing element comprises a flexible indexing finger, which finger is arranged to act on a gear wheel separate from and meshed with the powder container.

14. A device as claimed in claim 1, wherein the device is constructed and arranged to be used for delivering multiple doses of physiologically active agent in powdered form into the nasal cavity of a subject.

15. A device as claimed in claim 1, wherein the air reservoir is constructed and arranged to be freshly charged with air by the action of opening said closure in preparation for using the device for powder delivery.

16. A device as claimed in claim 1, further comprising a linkage between the reservoir and the closure.

17. A device as claimed in claim 16, wherein the closure is pivotable between its open and closed positions and said linkage is arranged to convert at least part of the pivoting movement of the closure into movement of part of the reservoir to cause air to be aspirated into the reservoir to recharge it.

18. A device as claimed in claim 1, wherein the reservoir comprises a cylinder with a piston slidably and sealably received therein.

19. A device as claimed in claim 1, wherein the reservoir is a bellows.

20. A device as claimed in claim 1, wherein the reservoir is displacable against a spring bias from a discharged reservoir condition to a charged reservoir condition so as to recharge the reservoir with air.

21. A device as claimed in claim 20, wherein a latching arrangement is provided to latch the reservoir in the charged reservoir condition.

22. A device as claimed in claim 21, wherein the latching arrangement is releasable to enable the reservoir to change from the charged reservoir condition to the discharged reservoir condition under the influence of said spring bias.

23. A device as claimed in claim 21, wherein the latching arrangement is arranged to be released by movement of said closure.

24. A device as claimed in claim 1, wherein the physiologically active agent in powdered form is a compound or composition of matter which, when administered to an organism, induces a desired pharmacologic or physiologic effect by local or systemic action.

25. A device as claimed in claim 1, wherein the physiologically active agent is a drug, biopharmaceutical, vaccine or gene therapy.

* * * * *